United States Patent
Bommarito et al.

(10) Patent No.: US 9,575,022 B2
(45) Date of Patent: Feb. 21, 2017

(54) ELECTRONIC INDICATOR FOR MONITORING EFFICACY OF A CLEANING CYCLE

(71) Applicant: 3M INNOVATIVE PROPERTIES COMPANY, St. Paul, MN (US)

(72) Inventors: G. Marco Bommarito, Stillwater, MN (US); Myungchan Kang, Woodbury, MN (US); Michael C. Palazzotto, Woodbury, MN (US); Timothy J. Nies, Stillwater, MN (US); Kelvin J. Witcher, Hudson, WI (US)

( * ) Notice: Subject to any disclaimer, the term of this patent is extended or adjusted under 35 U.S.C. 154(b) by 121 days.

(21) Appl. No.: 14/429,719

(22) PCT Filed: Oct. 2, 2013

(86) PCT No.: PCT/US2013/063062
§ 371 (c)(1),
(2) Date: Mar. 19, 2015

(87) PCT Pub. No.: WO2014/058673
PCT Pub. Date: Apr. 17, 2014

(65) Prior Publication Data
US 2015/0233852 A1    Aug. 20, 2015

Related U.S. Application Data

(60) Provisional application No. 61/710,846, filed on Oct. 8, 2012, provisional application No. 61/783,873, filed on Mar. 14, 2013.

(51) Int. Cl.
G01N 27/02    (2006.01)
G01N 27/22    (2006.01)

(52) U.S. Cl.
CPC ............ G01N 27/023 (2013.01); G01N 27/22 (2013.01)

(58) Field of Classification Search
CPC ........ A47L 15/4295; A47L 15/46; A61L 2/04; A61L 2/28; A61L 2202/17; A61L 2202/24; A61L 2202/122; A61L 2/183; A61L 2/186; A61B 1/00057; A61B 1/123; A61B 90/70; A61B 2090/702; A61B 2090/701; G01N 27/22; G01N 27/023; G01N 31/22; G01N 27/021; B08B 3/00; D06F 39/002
See application file for complete search history.

(56) References Cited

U.S. PATENT DOCUMENTS 4,571,543 A * 2/1986 Raymond ............ G01N 27/227
                                                257/414
4,710,233 A * 12/1987 Hohmann ............... A61L 2/035
                                                134/1

(Continued)

FOREIGN PATENT DOCUMENTS

CN    1799491        7/2006
CN    101539554      9/2009

(Continued)

OTHER PUBLICATIONS

Bratov, "New chemical sensor for detergents determination", 14 International Meeting on Chemical Sensors, 2012, pp. 1220-1222. XP055093304.

(Continued)

*Primary Examiner* — An T Nguyen

(57) ABSTRACT

An electronic indicator includes artificial soil and sensor. An electrical characteristic of the electronic indicator can vary due to a change in the volume of the artificial soil. In some embodiments, the electrical characteristic of the electronic indicator can be measured by an electrical characteristic reader and used to determine efficacy of a cleaning cycle.

24 Claims, 11 Drawing Sheets

(56) References Cited

U.S. PATENT DOCUMENTS

| | | | |
|---|---|---|---|
| 5,538,629 A | 7/1996 | Blaney | |
| 5,747,794 A | 5/1998 | Malchesky | |
| 5,851,489 A * | 12/1998 | Wolf | B01L 3/502715 |
| | | | 422/82.02 |
| 5,923,432 A * | 7/1999 | Kral | B08B 3/00 |
| | | | 134/113 |
| 6,083,755 A | 7/2000 | Buess | |
| 6,107,097 A | 8/2000 | Pfeifer | |
| 6,394,111 B1 * | 5/2002 | Jacobs | A61B 1/123 |
| | | | 134/113 |
| 6,395,551 B1 | 5/2002 | Kipke | |
| 6,447,990 B1 | 9/2002 | Alfa | |
| 7,246,627 B2 * | 7/2007 | Jacobs | A61L 2/183 |
| | | | 134/113 |
| 7,556,767 B2 * | 7/2009 | Lin | A61L 2/186 |
| | | | 422/28 |
| 7,563,329 B2 * | 7/2009 | Lin | A61B 1/00057 |
| | | | 134/18 |
| 7,691,329 B2 | 4/2010 | Potyrailo | |
| 8,083,924 B2 * | 12/2011 | Feldman | C12Q 1/001 |
| | | | 204/403.02 |
| 2001/0033805 A1 * | 10/2001 | Jacobs | A61B 1/123 |
| | | | 422/3 |
| 2005/0017728 A1 * | 1/2005 | Kaiser | G01N 27/221 |
| | | | 324/453 |
| 2006/0105467 A1 | 5/2006 | Niksa | |
| 2006/0218944 A1 | 10/2006 | He | |
| 2006/0218994 A1 * | 10/2006 | Lin | A61L 2/28 |
| | | | 73/60.11 |
| 2006/0219261 A1 * | 10/2006 | Lin | A61B 1/00057 |
| | | | 134/18 |
| 2007/0074742 A1 * | 4/2007 | Lin | A61L 2/183 |
| | | | 134/18 |
| 2007/0249054 A1 | 10/2007 | Doi | |
| 2008/0193631 A1 | 8/2008 | Kanamori | |
| 2013/0224849 A1 * | 8/2013 | Chandrapati | C12Q 1/22 |
| | | | 435/287.4 |
| 2015/0158056 A1 * | 6/2015 | Rastegar | H01L 21/67115 |
| | | | 134/1 |
| 2015/0233852 A1 * | 8/2015 | Bommarito | G01N 27/22 |
| | | | 340/691.1 |

FOREIGN PATENT DOCUMENTS

| | | |
|---|---|---|
| DE | 4437103 | 4/1996 |
| DE | 19534431 | 3/1997 |
| DE | 202007017612 | 3/2008 |
| EP | 1882772 | 1/2008 |
| JP | H06-88788 | 3/1994 |
| JP | 2006-346136 | 12/2006 |
| JP | 2007-244702 | 9/2007 |
| JP | 2009-39192 | 2/2009 |
| JP | 2009-61012 | 3/2009 |
| WO | WO 98-40736 | 9/1998 |
| WO | WO 2012-112482 | 8/2012 |

OTHER PUBLICATIONS

International Search Report for PCT International Application No. PCT/US2013/063062 mailed on Jan. 7, 2014, 4 pages.

* cited by examiner

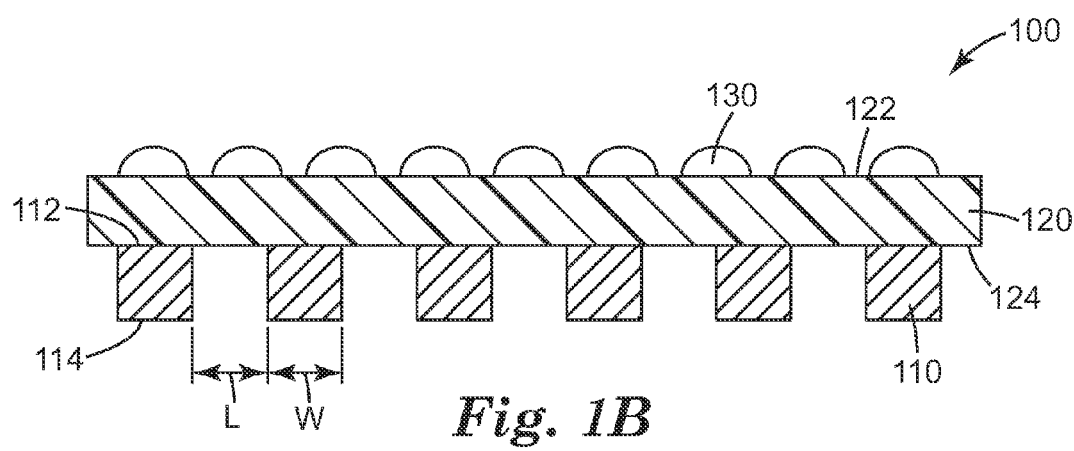
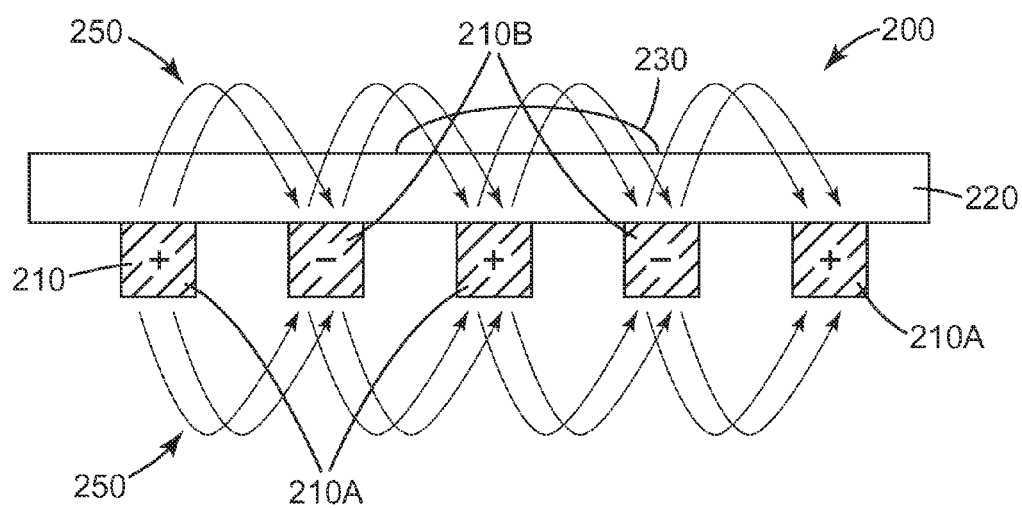
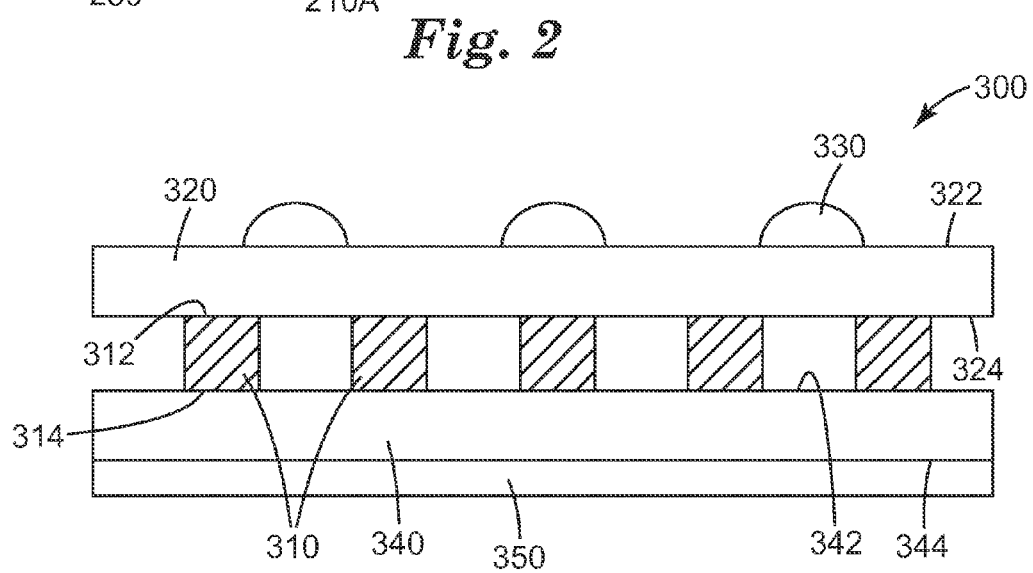

ELECTRONIC INDICATOR FOR MONITORING EFFICACY OF A CLEANING CYCLE

TECHNICAL FIELD

The present disclosure relates to electronic indicators used for monitoring cleaning process, including but not limited to, washing process and disinfection process. Some aspects of this disclosure relate to electronic indicators that can be disposed in a wash chamber during a wash and/or disinfection cycle and can be measured by electrical characteristics reader to evaluate the efficacy of the cleaning cycle.

SUMMARY

At least one aspect of the present disclosure features an electronic indicator to monitor efficacy of a cleaning cycle. The electronic indicator includes a barrier layer, artificial soil, and a sensor. The barrier layer includes a first dielectric material and has a first barrier surface and a second barrier surface, where the first barrier surface is opposite to the second barrier surface. A volume of wash-removable artificial soil is disposed on at least a portion of the first barrier surface. The sensor has a first major sensor surface and an opposing second major sensor surface, where the first major sensor surface is adjacent to the second barrier surface. The electrical characteristic of the electronic indicator varies in response to a change in the volume of the artificial soil.

At least one aspect of the present disclosure features a wash efficacy measurement system comprising an electronic indicator and an electrical characteristic reader. The electronic indicator is configured to be disposed in a wash chamber during a cleaning cycle. The electronic indicator includes a barrier layer, artificial soil, and a sensor. The barrier layer includes a dielectric material. The barrier layer has a first barrier surface and a second barrier surface, where the first barrier surface is opposite to the second barrier surface. A volume of wash-removable artificial soil is disposed on at least a portion of the first barrier surface. The sensor has a first major sensor surface and an opposing second major sensor surface, where the first major sensor surface is adjacent to the second barrier surface. The sensor is configured to produce a sensor signal associated with an electrical characteristic of the electronic indicator when the electronic indicator is measured by an electrical characteristic reader. The electrical characteristic of the electronic indicator varies in response to a change in the volume of the artificial soil. The electrical characteristic reader is configured to measure an after-wash electrical characteristic of the electronic indicator after the cleaning cycle, where the after-wash electrical characteristic of the electronic indicator indicates an efficacy of the cleaning cycle.

At least one aspect of the present disclosure features an electronic indicator to monitor efficacy of a cleaning cycle. The electronic indicator includes a barrier layer, artificial soil, a sensor, and an insulating layer. The barrier layer includes a first dielectric material and has a first barrier surface and a second barrier surface, where the first barrier surface is opposite to the second barrier surface. A volume of wash-removable artificial soil is disposed on at least a portion of the first barrier surface. The sensor has a first major sensor surface and an opposing second major sensor surface, where the first major sensor surface is adjacent to the second barrier surface. The insulating layer includes a second dielectric material and has a first insulating layer surface and an opposing second insulating layer surface, where the first insulating layer surface is adjacent to the second major sensor surface and covers at least a portion of the second major sensor surface. The electrical characteristic of the electronic indicator varies in response to a change in the volume of the artificial soil.

At least some aspects of the present disclosure feature methods for measuring wash efficacy comprising the steps of: (1) disposing an electronic indicator in a wash chamber during a cleaning cycle, (2) measuring an after-wash electrical characteristic of the electronic indicator after the cleaning cycle; and (3) recording the after-wash electrical characteristic of the electronic indicator. The electronic indicator typically includes a sensor and a volume of wash-removable artificial soil disposed on at least a portion of a surface of the electronic indicator. The sensor is configured to produce a sensor signal associated with an electrical characteristic of the electronic indicator, where the electrical characteristic of the electronic indicator varies in response to a change in the volume of the artificial soil.

BRIEF DESCRIPTION OF THE DRAWINGS

The accompanying drawings are incorporated in and constitute a part of this specification and, together with the description, explain the advantages and principles of the invention. In the drawings.

FIG. 1B illustrates schematically a cross-sectional view of the electronic indicator illustrated in FIG. 1A;

FIG. 2 illustrates schematically a partial cross-sectional view of an electronic indicator having an interdigitated electrode sensor;

FIG. 3A illustrates schematically a partial cross-sectional view of an exemplary embodiment of an electronic indicator;

DETAILED DESCRIPTION

Figure 1A:
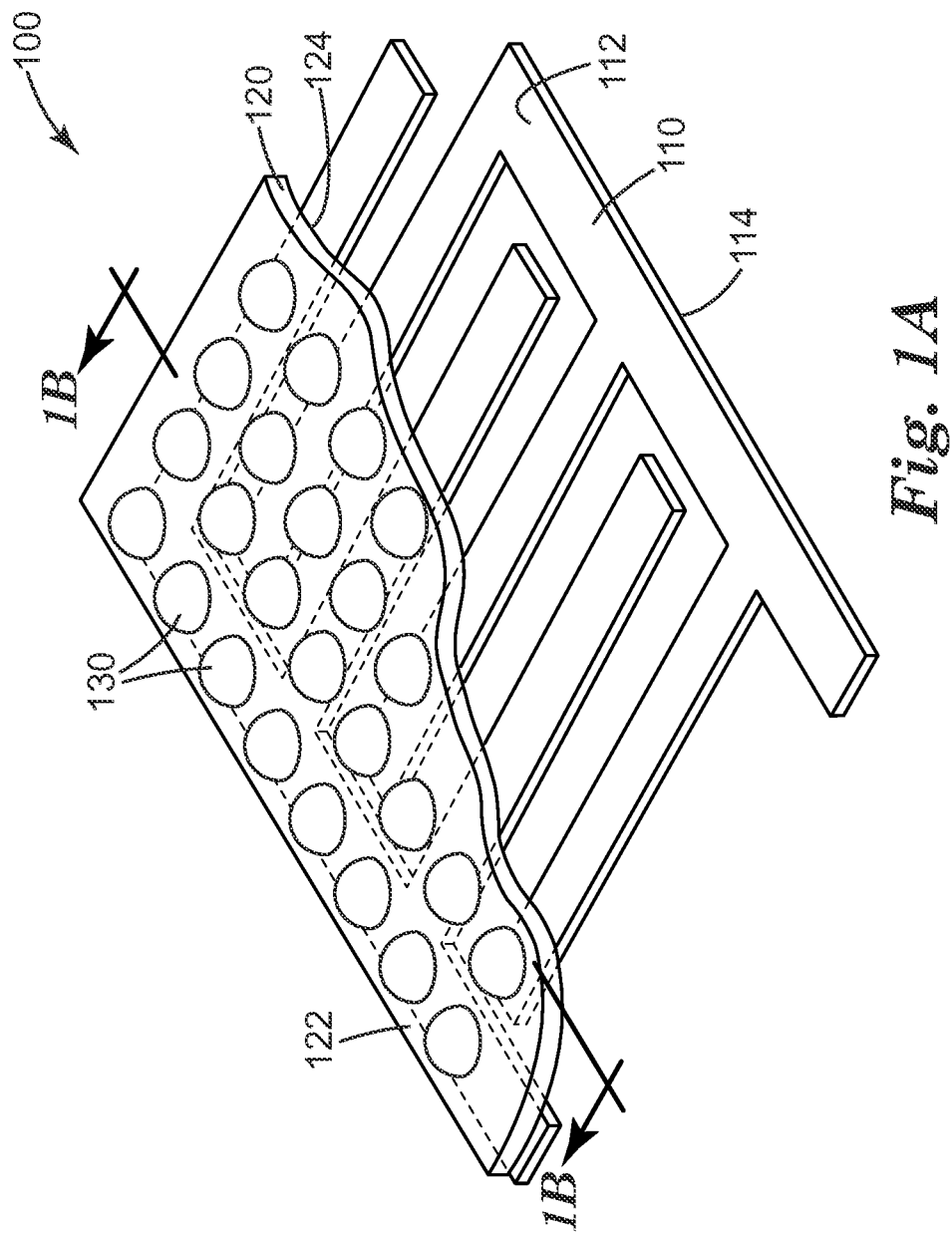
FIG. 1A illustrates schematically a perspective view of an exemplary embodiment of an electronic indicator.

Decontamination is a process of cleaning objects using physical and/or chemical means. Hospital or other health care facilities often use heat, either steam or hot water, to decontaminate medical devices. Additionally, washing in hot water at proper temperature and for a sufficient amount of time provides a broad disinfecting effect. Disinfection is a process capable of destroying and/or removing pathogenic microorganisms. Disinfection processes are intended to destroy or prevent growth of microorganisms capable of causing infections. The microorganisms include, for example, vegetative bacteria, pathogenic fungi, and specifically tested viruses. Disinfection process can be a thermal disinfection process, a chemical disinfection process using chemical disinfectant(s), or a combination thereof. Washing in hot water is a popular way for thermal disinfection due to its low cost and personal and environmental safety.

Reusable devices or articles often require wash and disinfection after each use. It is important to monitor and ensure the efficacy of such wash and disinfection in cleaning theses devices or articles, especially in cleaning devices or articles to be used in medical, dental, pharmaceutical and veterinary practices. Fluid, such as hot water or steam, is often used in the wash and thermal disinfection process. During a wash process, cleaning agents and enzymes may also be used in the hot water. An effective wash process may require the fluid to be heated to an appropriate temperature range to activate the cleaning agents and enzymes for a sufficiently long time period. A thermal disinfection process may require the fluid to be heated to a minimum temperature and for an adequate time period. For example, in ISO 15883-1, "A" value, a value of equivalent time in seconds at 80° C., is used to evaluate a disinfection efficacy. Current indicators in use often require visual inspections that lead to inaccurate results because visual inspection cannot quantify how much soil is left on the indicators. Additionally, visual inspection is a manual process that is subject to operator error (i.e., logging the wrong data, log to the wrong record, etc.).

Aspects of this disclosure are directed to embodiments of an electronic indicator that can be measured by an electrical characteristic reader, where the measured value can be used to evaluate efficacy of a cleaning (i.e., wash, disinfection, etc.) cycle. In other words, at least some aspects of the present disclosure are directed to machine readable electronic indicator of efficacy of cleaning cycles. As used herein, an electrical characteristic reader can be any device, instrument, or circuit that can be used to measure an electrical characteristic, including but not limited to, a capacitance meter, an impedance analyzer, an LCR meter, and a digital multimeter. In some embodiments, an electronic indicator includes an electronic sensor, artificial soil, and a barrier layer between the electronic sensor and the artificial soil. The barrier layer typically includes dielectric material. In some cases, the electrical characteristic (i.e. capacitance, impedance, inductance, resistance, admittance, current, etc.) of the electronic indicator is typically affected by the attributes of the indicator, for example, the sizes and arrangements of electrode(s) used in the electronic sensor, the volume of the artificial soil, the thickness of the barrier layer, and other attributes of the indicator. The volume of artificial soil typically changes during a cleaning cycle (i.e., the volume is reduced) and the electrical characteristic may be varied by the change of the volume of artificial soil. For example, the capacitance of the electronic indicator decreases when the volume of artificial soil decreases during a cleaning cycle. In some embodiments, an electronic indicator is placed into a wash chamber before a cleaning cycle and the electrical characteristic of the electronic indicator can be read by an electrical characteristic reader after the cleaning cycle, which can be used to evaluate the efficacy of the cleaning cycle.

Artificial soil encompasses a composition comprising a target analyte (i.e., an acid, a base, a nucleotide, a protein, a nucleic acid, a carbohydrate, or hemoglobin), where the presence and/or the residual amount of the target analyte after a cleaning cycle can be used to evaluate the efficacy of the cleaning cycle. In some embodiments, the artificial soil can be made from commercially available test soil. For example, the artificial soil can be a mixture of 9 mL sterile water added to a single vial of Artificial Test Soil ATS-9 available from Healthmark Industries Company, Inc., Fraser, Mich., USA. In some embodiments, the artificial soil composition further can comprise an optional dye in an amount sufficient to be optically detectable. In some cases, the artificial soil further comprises a polymeric binder. In some implementations, the artificial soil can be prepared by dissolving and/or making a homogeneous dispersion of the target analyte, polymeric binder, and optional dye in a suitable solvent (i.e., water, alcohol, or mixtures thereof), applying the mixture to a surface (i.e., by spraying, dip-coating, or other coating processes known in the art) of a substrate, and removing at least a portion of the solvent (i.e., substantially all of the solvent) to obtain a dried coating on the substrate.

Embodiments of the present disclosure are directed to electronic indicators comprising wash-removable artificial soil. Generally, wash-removable artificial soil refers to artificial soil that can be removed during a cleaning process such that the remaining volume of artificial soil is reduced or eliminated. In some embodiments, the remaining volume of artificial soil is an indication of the efficacy of the wash process.

FIG. 1A illustrates schematically a perspective view of an exemplary embodiment of an electronic indicator 100. FIG. 1B illustrates schematically a cross-sectional view of the electronic indicator 100 illustrated in FIG. 1A (cross section at line 1B). In some embodiments, the electronic indicator 100 includes an electronic sensor 110, a barrier layer 120, and artificial soil 130. The electronic sensor 110 can include one or more electrodes. The barrier layer 120 can include one or more dielectric materials. Dielectric material can include, for example, polymeric material, air, glass, ceramic/inorganic material, plastic, and the like. Polymeric material can include but is not limited to polyester, polyimide, polyamide-imide, polyvinyl chloride (PVC), poly isobutene (butyl rubber), polytetrafluoroethylene (PTFE), fluorinated ethylene propylene (FEP), polyvinylidene chloride (PVDC), thermoplastic chlorofluoropolymers such as polytrifluorochloroethylene (PTFCE; or Kel-F81), polyethylene terephthalate (PET), polypropylene, polyethylene, polyphenylene sulfide, polyethylene naphthalate, polycarbonate, silicone rubber, ethylene propylene diene rubber (EPDM), polyurethane, acrylate polymers, silicones, natural rubber, epoxies, and synthetic rubber adhesives. Ceramic/inorganic material can include but is not limited to metal oxide (i.e., silicon oxide, aluminum oxide, titanium oxide, zirconium oxide, chromium oxide, tantalum oxide, vanadium oxide etc.).

The barrier layer may have a thickness in the range of 5 nm to 5 mm. In some cases, the barrier layer 120 may be a continuous slab, layer, or film. In some other cases, the barrier layer 120 may include an adhesive layer, for example, an epoxy layer, to attach to the sensor 110. In some configurations, the barrier layer 120 may be an adhesive layer. In some cases, the barrier layer 120 has low moisture permeability. In some implementations, the barrier layer can be constructed to provide sufficient physical strength and integrity for the construction of the electronic indicator 100. The artificial soil 130 can include commercially available artificial test soil (ATS) or proprietary artificial soil.

In some embodiments, the barrier layer 120 can have a first barrier surface 122 and a second barrier surface 124, where the first barrier surface 122 is opposite to the second barrier surface 124. The artificial soil 130 is disposed on at least a portion of the first barrier surface 122, where the volume of the artificial soil 130 decreases during a washing process. The sensor 110 can have a first major sensor surface 112 and an opposing second major sensor surface 114, wherein the first major sensor surface 112 is adjacent to the second barrier surface 124. The sensor 110 is configured to produce a sensor signal associated with an electrical characteristic of the electronic indicator when the electronic indicator is measured by an electrical characteristic reader. The electrical characteristic of the electronic indicator can vary in response to a change in the volume of the artificial soil. For example, when the amount of artificial soil decreases during a cleaning cycle, the total impedance of the electronic indicator can increase. The electrical characteristic can be represented by impedance, capacitance, inductance, resistance, other electrical characteristics, and a combination thereof.

The sensor 110 can include electrodes. In some configurations, the sensor 110 can include electrodes that are generally on the same planar surface. In some other configurations, the sensor 110 can include electrodes that are not on the same planar surface. In some cases, as illustrated in FIG. 1A and FIG. 1B, the electrodes can be metal traces. In FIG. 1B, "L" denotes the distance between two adjacent electrodes, which is also referred to as electrode spacing. "W" denotes the width of an electrode, which is also referred to as electrode line width or electrode "metal trace" width. Electrodes can include any suitable conductive material. In some cases, electrodes can include combinations of different materials (conductive and/or nonconductive), as different layers or as a mixture, as long as sufficient overall conductivity is provided. For example, the electrode material may include a constant resistivity of less than about $10^{-2}$ ohms-meter. Examples of materials that can be used in electrodes include, but are not limited to, organic materials, inorganic materials, metals, alloys, and various mixtures and composites comprising any or all of these materials. In certain embodiments, coated (for example, vapor coated, sputter coated, etc.) metals or metal oxides, or combinations thereof, may be used. Suitable conductive materials include, for example, aluminum, tin, indium-tin oxide, gold, silver, platinum, palladium, copper, and the like. In some cases, different electrodes may include the same material. In some other cases, different electrodes may include different materials.

The sensor 110 can include a capacitance sensor, an impedance sensor, other electrical sensors, or a combination thereof. In some embodiments, the volume of the artificial soil 130 on the active area of the electronic indicator 100 can change the overall capacitance of the electronic indicator 100. As used here, an active area of an electronic indicator refers to the area that the sensing component covers. For example, it can be the area where the sensitivity of the electrical field of electrodes is greater than a certain threshold. One of the factors that will determine the amount of change in the electrical characteristic is the dielectric properties of the artificial soil 130. The electronic indicator can be used to determine how much artificial soil 130 remains on the surface after a cleaning cycle and/or how much artificial soil 130 is washed away.

In some configurations, the artificial soil 130 can be arranged as a layer to cover at least a portion of the first barrier surface 122. In some other configurations, the artificial soil 130 can be also arranged into soil areas as illustrated in FIG. 1A. The areas can be in the shapes of circles, oval, or other shapes. In yet other configurations, the artificial soil 130 can be arranged to a layer (i.e., soil layer) covering at least a portion of the first barrier surface 122 and additionally arranged into areas that are disposed on the soil layer.

FIG. 2 illustrates schematically a partial cross-sectional view of an electronic indicator having an interdigitated electrode sensor 200. The electronic indicator 200 includes a sensor 210, a barrier layer 220, and artificial soil 230. The sensor 210 can include interdigitated electrodes. In some cases, as illustrated in FIG. 2, the sensor 210 can include two electrodes 210A and 210B arranged interdigitated manner. In some implementations, when the electronic indicator 200 is measured by an electrical characteristic reader, each of the two electrodes 210A and 210B can be applied with direct current (DC) or alternating current (AC) potentials by the reader. For example, electrode 210A can be applied with a DC positive potential and electrode 210B can be applied with a DC negative potential. As another example, electrode 210A can be applied with an AC positive electric potential and electrode 210B can be applied with an AC negative electric potential at one point in time. In some implementations, the sensor 210 can include an interdigitated electrode sensor having two electrodes. In some other implementations, the sensor 210 can include an interdigitated electrode sensor having three or more electrodes. During measurement, when potential difference is applied to electrodes, the electronic indicator 200 can generate a sinusoidal electric field extending normal to the major surface of the sensor, illustrated as 250. In some cases, the field strength decreases rapidly from the major sensor surface.

As used herein, interdigitated encompasses any arrangement comprising at least two electrodes present in an interdigitated configuration. Such configurations include interdigitated comb patterns (as depicted in FIG. 2), as well as interdigitated spiral patterns, interdigitated serpentine patterns, or the like. In some embodiments, at least two electrodes are present in a largely coplanar interdigitated arrangement with a dielectric layer present in proximity to the electrodes such that an electric field is established between the electrodes. The dielectric layer/material may be provided between the electrodes (i.e. in the plane of the two electrodes and interposed in the closest linear path between any two points of approach of the first and second electrodes). Alternatively, the dielectric layer/material may be provided such that, while not coplanar with the electrodes, the dielectric material is exposed at least to the fringing electric field that is established between adjacent sections of the two electrodes. In still another alternate embodiment, the dielectric layer may be provided in both locations. In some embodiments, at least two electrodes are present in an interdigitated arrangement while the electrodes are on different planar surfaces with a dielectric layer present in proximity to the electrodes.

Interdigitated electrodes can be provided by the deposition of conductive material in two interdigitated patterns by any of the methods (e.g. masked vapor deposition, screen-printing, ink-jet printing) that are well known for patterned deposition of materials. The particular geometric/dimensional properties of the electrode patterns (spacing, height, length etc.) may be designed as desired.

FIG. 3A illustrates schematically a partial cross-sectional view of an exemplary embodiment of an electronic indicator 300. The electronic indicator 300 includes a sensor 310, a barrier layer 320, artificial soil 330, an optional insulating layer 340, and an optional shielding layer 350. The sensor 310 can include one or more electrodes that can produce sensor signals indicating an electrical characteristic (i.e., impedance, capacitance, etc.) of the electronic indicator 300 when it is measured by an electrical characteristic reader (i.e., impedance analyzer, capacitance reader, etc.). In some configurations, the barrier layer 320 can include any dielectric material that is feasible to provide insulation between the sensor 310 and the artificial soil 330. In some configurations, the barrier layer 320 can be a relative thin layer so the indicator 300 is sensitive to the volume change of the artificial soil. The optional insulating layer 340 can include any dielectric material that is suitable for physical and electrical requirement. The material used in the insulating layer 340 can include the same materials as listed above for the barrier layer. For example, the insulating layer 340 can include a silicone based pressure sensitive adhesive coated on a polyester substrate. In some cases, the insulating layer 340 can be a relative thick layer to provide physical support for the electronic indicator 300.

In some embodiments, the insulating layer can have low moisture permeability. In some configurations, the insulating layer 340 can be chosen to be thick enough to ensure that the sensing field created by the electrodes (i.e., depicted as 250 in FIG. 2) is fully contained within the insulating layer 340. Such configurations may help increase electronic indicator's sensitivity to the changes in the volume of artificial soil 330. In some embodiments, the sensitivity of an electronic indicator can be indicated by the magnitude of changes in the electrical characteristic of the electronic indicator 300 caused by changes in the volume of artificial soil 330. In some embodiments, the barrier layer 320 and the insulating layer 340 may have the same materials. In some other embodiments, the barrier layer 320 and the insulating layer 340 may not have the same materials.

In some embodiments, the barrier layer 320 can have a first barrier surface 322 and a second barrier surface 324, where the first barrier surface 322 is opposite to the second barrier surface 324. The artificial soil 330 is disposed on at least a portion of the first barrier surface 322, where the volume of the artificial soil 330 typically decreases during a cleaning process (i.e., a wash process, a disinfection process, or a combination thereof). The sensor 310 can have a first major sensor surface 312 and an opposing second major sensor surface 314, wherein the first major sensor surface 312 is adjacent to the second barrier surface 324. The insulating layer 340 can have a first insulating layer surface 342 and an opposing second insulating layer surface 344, wherein the first insulating layer surface 342 is adjacent to the second major sensor surface 314 and covers at least a portion of the second major sensor surface 314.

In some embodiments, the electronic indicator 300 can include a shielding layer 350. The shielding layer 350 may include any conductive material, for example, conductive organic materials, inorganic materials, metals, alloys, and various mixtures. Suitable conductive materials include for example aluminum, tin, indium-tin oxide, gold, silver, platinum, palladium, copper, and the like. The shielding layer 350 can reduce electrical interference when the electrical indicator 300 is being measured. The shielding layer may include a conductive material disposed on at least a portion of the second insulating layer surface 344. In some cases, the shielding layer 350 can function as a grounding electrode for the sensor 310.

Figure 3B:
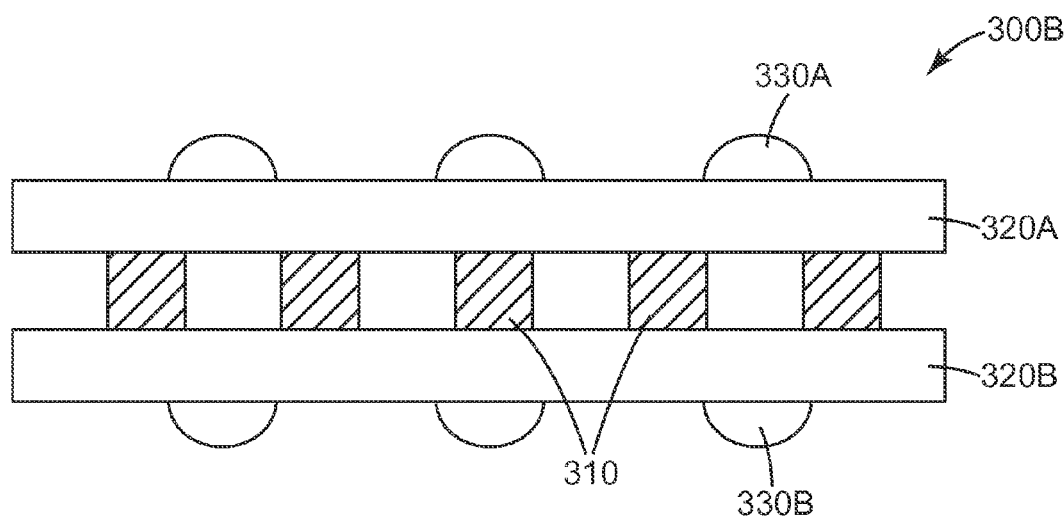
FIG. 3B illustrates schematically a partial cross-sectional view of another exemplary embodiment of an electronic indicator.

FIG. 3B illustrates schematically a partial cross-sectional view of another exemplary embodiment of an electronic indicator 300B. In some configurations, the electronic indicator 300B can include a sensor 310, a first barrier layer 320A, first artificial soil 330A that is disposed on the first barrier layer 320A, a second barrier layer 320B, and second artificial soil 330B that is disposed on the second barrier layer 320B. In such configuration, an electrical characteristic (i.e., impedance, capacitance, resistance, inductance, etc.) of the indicator 300B can be varied by both the volume of the first artificial soil 330A and the volume of the second artificial soil 330B.

Figure 4A:
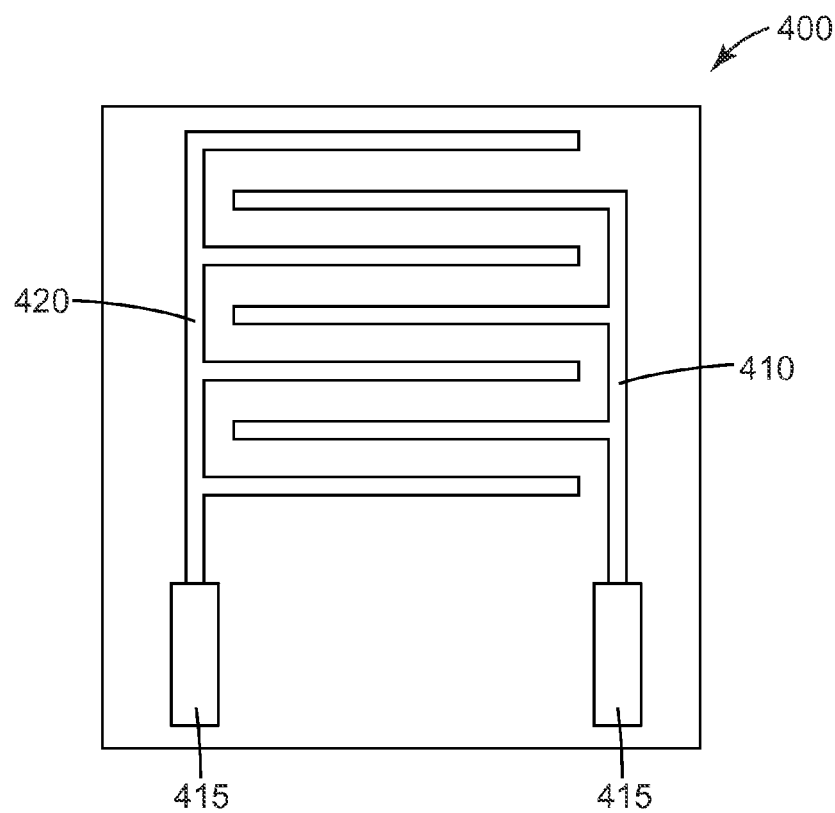
FIG. 4A illustrates schematically a top view of an exemplary embodiment of an interdigitated electrode sensor.

FIG. 4A illustrates schematically a top view of an exemplary embodiment of an interdigitated electrode sensor 400. In some embodiments, the interdigitated electrode sensor 400 can include electrodes 410 and 420 that are arranged as illustrated in FIG. 4A. Contact pads 415 are optional components and include conductive materials (i.e., copper, etc.), which can be used to allow better and easy connection during measurement.

Figure 4B:
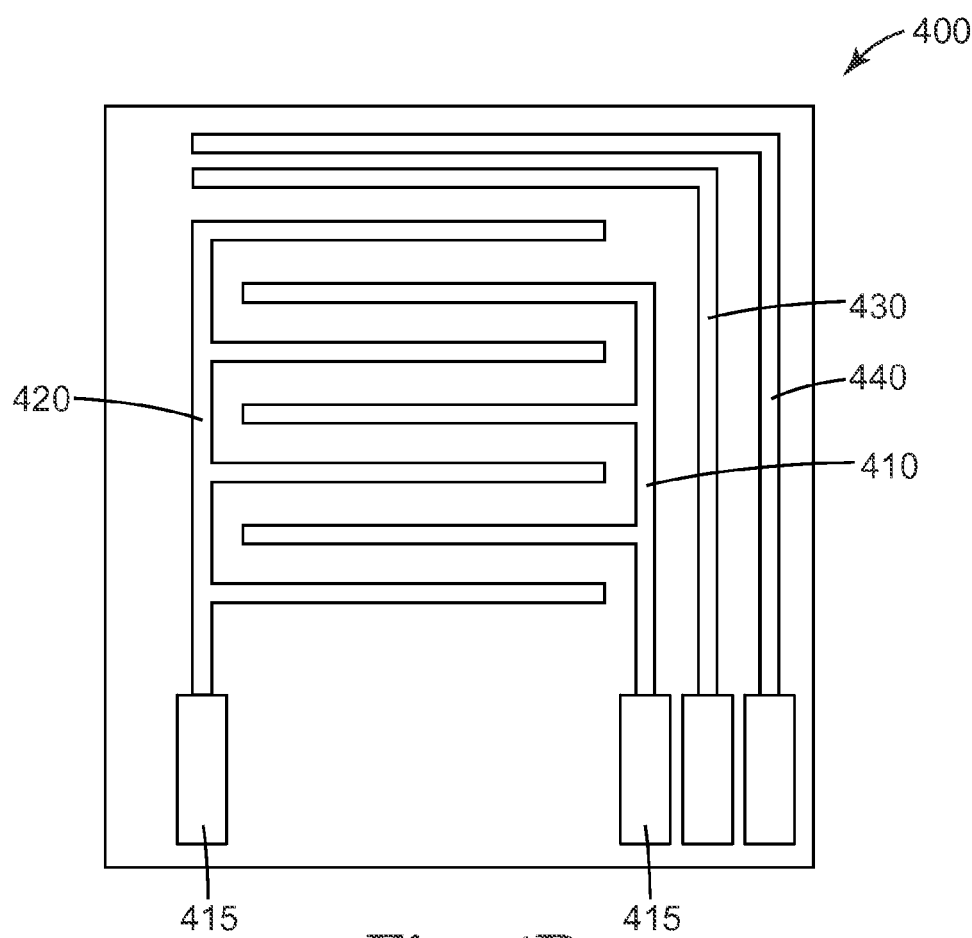
FIG. 4B illustrates schematically a top view of another exemplary embodiment of an interdigitated electrode sensor.

FIG. 4B illustrates schematically a top view of another exemplary embodiment of an interdigitated electrode sensor 400. In some embodiments, the interdigitated electrode sensor 400 can include sensing electrodes 410 and 420, optional guard electrode 430, and optional ground electrode 440. Contact pads 415 are optional components that can be used to allow better and easy connection during measurement. The guard electrode 430 can provide shielding of sensing electrodes (i.e., electrodes 410 and 420) in the plane of the sensor. The ground electrode 440 can provide shielding of the guard electrodes (i.e. guard electrode 430) and/or other electrodes. In some embodiments, the length of the sensor 400 can be in the range of 0.5 cm to 25 cm and the width of the sensor 400 can be in the range of 0.5 cm to 25 cm. A typical length of the sensor 400 can be in the range of 1 cm to 10 cm and a typical width of the sensor 400 can be in the range of 0.5 cm to 5 cm. In some embodiments, the electrode spacing between adjacent metal traces for interdigitated electrodes can be 5 µm to 1 cm. Typical electrode spacing between adjacent metal traces is 10 µm to 500 µm. A more typical spacing between adjacent metal traces is 50 µm to 200 µm. In some embodiments, the electrode line width of metal traces for interdigitated electrodes can be 5 µm to 1 cm. A typical line width of metal traces is 10 µm to 500 µm. A more typical width of metal traces is 50 µm to 200 µm. In such configurations, tens or hundreds of metal traces are included in the sensor 400.

Figure 5:
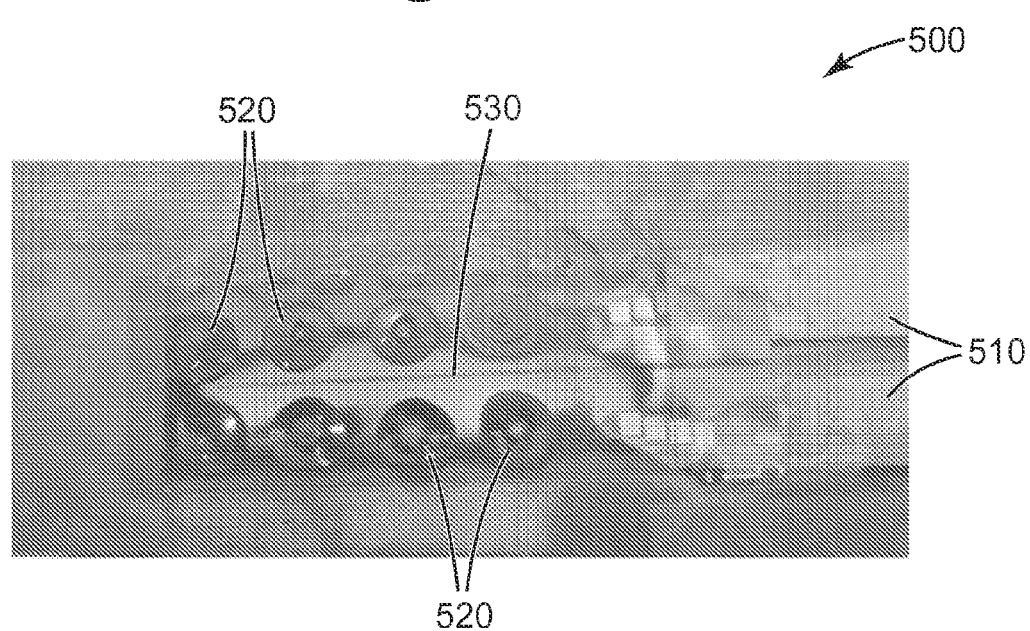
FIG. 5 is a picture of an exemplary embodiment of an electronic indicator.

FIG. 5 is a picture of an exemplary embodiment of an electronic indicator 500. In one embodiment, the electronic indicator 500 includes two copper strips 510 that can be used to connect the electronic indicator 500 to a measuring device. The electronic indicator 500 also includes a polyimide barrier layer 530 and eight individual spot coatings 520 of artificial soil disposed on top of the barrier layer 530.

As a specific example illustrated in FIG. 5, the electrode spacing and electrode line width of the electrodes is 75 μm and the area with metal traces is 2.44 cm×1.02 cm (i.e., active area of the electronic indicator). The barrier layer uses a 25 μm thick polyimide films. The indicator 500 can be connected to impedance analyzer through copper tapes and additional wires. Transparent tapes can be applied to cover and insulate copper electrodes. In an exemplary implementation, the indicator 500 can be placed on a hot plate with the polyimide side up. The hot plate can be maintained at a high temperature (i.e., 60° C.) in order to expedite the drying process of artificial soils. An amount of 10 μL of artificial soil per spot can be delivered using a micropipette. The size of artificial soil spot can be generally uniform.

Figure 6:
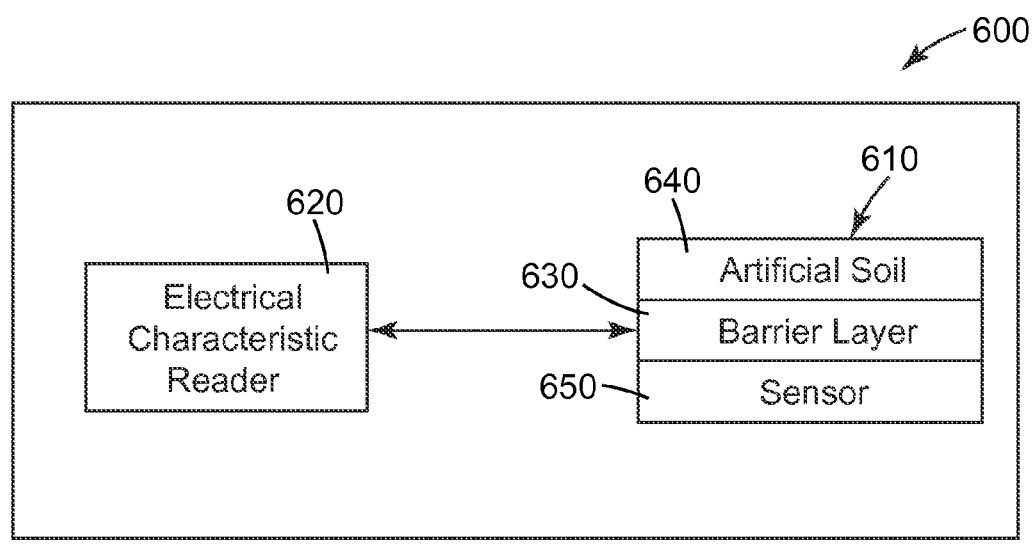
FIG. 6 is a block diagram for an exemplary embodiment of a wash efficacy measurement system.

FIG. 6 is a block diagram for an exemplary embodiment of a wash efficacy measurement system 600. The wash efficacy measurement system 600 includes an electronic indicator 610 and an electrical characteristic reader 620. The electronic indicator 610 is configured to be disposed in a wash chamber during a cleaning cycle (i.e., wash or disinfection, etc.). For example, the electronic indicator 610 can be placed in the wash chamber of a GETINGE 46-series washer disinfector available from Getinge USA, Inc., Rochester, N.Y., which can be used to clean (i.e., wash and disinfect) surgical instruments before they are sterilized. The electronic indicator 610 can be implemented by any of the above mentioned embodiments. In some embodiments, the electronic indicator 610 includes a barrier layer 630 having a first barrier surface and an opposing second barrier surface; a volume of wash-removable artificial soil 640 disposed on at least a portion of the first barrier surface; and a sensor 650 having a first major sensor surface and an opposing second major sensor surface. The barrier layer 630 includes a dielectric material. The volume of the artificial soil typically decreases during a cleaning cycle. The first major sensor surface is adjacent to the second barrier surface. The sensor 650 is configured to produce a sensor signal associated with an electrical characteristic of the electronic indicator 610 when the electronic indicator 610 is measured by an electrical characteristic reader. The electrical characteristic of the electronic indicator 610 varies in response to a change in the volume of the artificial soil 640. The electrical characteristic reader 620 is configured to measure an after-wash electrical characteristic of the electronic indicator after the cleaning cycle, where the after-wash electrical characteristic of the electronic indicator can indicate an efficacy of the cleaning cycle.

In some implementations, the sensor 650 can include an interdigitated electrode sensor. In some cases, the interdigitated electrode sensor can include two electrodes, where the electrical characteristic reader 620 can provide potentials to the two electrodes. In some embodiments, the electrical characteristic reader 620 can be further configured to measure a before-wash electrical characteristic of the electronic indicator 610 before the cleaning cycle, wherein the efficacy of the cleaning cycle is determined based on the before-wash electrical characteristic of the electronic indicator 610 and the after-wash electrical characteristic of the electronic indicator 610.

In some cases, the before-wash electrical characteristic of the electronic indicator 610 is measured when the electronic indicator 610 does not have artificial soil. In some implementations, the efficacy of the cleaning cycle (Efficacy) can be represented by:

$$\text{Efficacy} = E_{After} - E_{BeforeNoSoil}, \quad (1)$$

where $E_{After}$ denotes the electrical characteristic of the electronic indicator 610, previously loaded with artificial soil, measured by the electrical characteristic reader 620 after the cleaning cycle, and $E_{BeforeNoSoil}$ denotes the electrical characteristic measured before the cleaning cycle where the electrical indicator does not have artificial soil applied to its surface. In general, the magnitude of Efficacy close to 0 indicates an adequate cleaning cycle. In some implementations, $E_{BeforeNoSoil}$ can be a predetermined value for electronic indicators with identical configurations.

In some other cases, the before-wash electrical characteristic of the electronic indicator 610 is measured when the electronic indicator 610 has artificial soil applied to its surface. In some implementations, the efficacy of the cleaning cycle (Efficacy) can be represented by:

$$\text{Efficacy} = E_{BeforeWithSoil} - E_{After}, \quad (2)$$

where $E_{After}$ denotes the electrical characteristic of the electronic indicator 610, previously loaded with artificial soil, measured by the electrical characteristic reader 620 after the cleaning cycle, and $E_{BeforeWithSoil}$ denotes the electrical characteristic measured before the cleaning cycle where the electrical indicator has artificial soil applied to its surface. In some cases, if the barrier layer used between the sensor and the artificial soil is highly insulating, a capacitance measurement can be suitable to detect changes in the volume of artificial soil. In some other cases, if the barrier layer used between the sensor and the artificial soil is semi-insulating, the electrical characteristic sensitive to the change of the soil volume can include resistance. In some implementations, $E_{BeforeWithSoil}$ can be a predetermined value for electronic indicators with identical configurations.

In some exemplary embodiments, the electronic indicator used to monitor the efficacy of a cleaning cycle can include a capacitor sensor. In such embodiments, an after-wash capacitance ($C_{After}$) of the electronic indicator can be measured by a capacitor meter after the cleaning cycle to determine the efficacy of the cleaning cycle. In some cases, a before-wash capacitance ($C_{BeforeWithSoil}$ or $C_{BeforeNoSoil}$) of the electronic indicator with or without soil can be measured by a capacitor meter before the cleaning cycle, where the efficacy of the cleaning cycle can be evaluated based on both the after-wash capacitance and the before-wash capacitance. In some implementations, the efficacy of the cleaning cycle can be indicated by the differentials between the after-wash capacitance and the before-wash capacitance.

In some cases, a wash efficacy monitor system can use an electronic indicator to monitor the efficacy of a cleaning cycle in real-time. In such cases, the electronic indicator can connect to an electronic characteristic reader during a cleaning cycle, for example, via an insulated wire. The electrical characteristic of the electronic indicator can be measured continuously, at certain cycle time, and/or with a certain sample rate by the electronic characteristic reader. The wash efficacy monitor system can analyze the measured data and generate a signal indicative of the wash efficacy, for example, by a processor-based device. In some cases, the processor-based device can be the electrical characteristic reader and/or a separate device. Such signal can be used to adjust the cleaning cycle, for example, to expand or shorten the cycle time or to change the configuration of the cleaning cycle.

At least some aspects of the present disclosure are directed to methods for measuring wash efficacy. First, dispose an electronic indicator in a wash chamber during a cleaning cycle (step 1210). The electronic indicator typically includes a sensor and a volume of wash-removable artificial soil disposed on at least a portion of a surface of the electronic indicator. The sensor is configured to produce a sensor signal associated with an electrical characteristic of the electronic indicator, where the electrical characteristic of the electronic indicator varies in response to a change in the volume of the artificial soil. Next, measure an after-wash electrical characteristic of the electronic indicator after the cleaning cycle (step 1220). A wash efficacy monitoring system records the after-wash electrical characteristic of the electronic indicator (step 1230) in, for example, a device memory, a file, a database, or the like.

In some embodiments, the system determines an efficacy of the cleaning cycle based on the after-wash electrical characteristic of the electronic indicator. In some embodiments, a plurality of after-wash electrical characteristic of electronic indicators are collected for a specific cleaning equipment, a specific position within a cleaning equipment, equipment of a specific organization, or other levels. In some cases, a threshold electrical characteristic can be determined based on the plurality of after-wash electrical characteristic of electronic indicators, where the threshold electrical characteristic can be used to determine efficacy of a cleaning cycle. For example, a measured after-wash electrical characteristic is compared with the threshold electrical characteristic to determine efficacy of the cleaning cycle.

In some cases, an action limit can be defined based on a plurality of after-wash electrical characteristic of electronic indicators collected under a controlled condition, where the action limit is associated with a predetermined action. Action limit refers to a threshold electrical characteristic measured after a cleaning cycle under a controlled condition (i.e., a selected volume of artificial soil with a pre-defined equipment condition and/or decontamination process), which indicates a particular sub-process or a series of sub-processes failed to remove or inactivate an acceptable amount of soil from the article. Action limits can be used to determine what actions (e.g., re-processing the load, equipment maintenance), if any, should be taken as a result of inadequate removal of artificial soil from electronic indicators. Action limits for controlling a multi-step cleaning, washing, and decontamination process are disclosed in International Patent Publication No. WO 2012/112482, which is incorporated herein by reference in its entirety.

In some cases, a system can compare the after-wash electrical characteristic of the electronic indicator to an action limit and provide a signal indicative of a predefined action based on the comparison. For example, if an after-wash electrical characteristic of the electronic indicator is above or below an action limit requiring equipment maintenance (e.g., adding detergent), the system can provide a warning message of "equipment maintenance" to users. In some embodiments, the system can collect electrical characteristic in real time during a cleaning cycle, compare the value or a set of values with the action value, and provide a signal indicative of a predefined action based on the comparison. For example, the system can inform the user of "equipment maintenance" before the completion of a cleaning cycle.

Several factors can affect the sensitivity of the sensor used in an electronic indicator, where the sensitivity is often associated with the change in the electrical characteristic verse the change in the amount of artificial soil. For example, for a fixed change in the amount of artificial soil (i.e., 20 µL reduction, etc.), an electronic indicator having the larger change in the electrical characteristic (i.e., 20 pF reduction in capacitance v. 10 pF reduction in capacitance) will have a higher sensitivity. The first factor is the characteristics of the area covered by the artificial soil. For example, the shape, size, position, and other attributes of the sensor's coating area may affect the sensitivity of the sensor. The second factor is the artificial soil coating thickness. In some cases, the sensor can be most sensitive to the portion of the soil coating closest to the barrier layer's surface. In some cases, a very thick soil coating will eventually saturate the sensor's response. Because the sensor can be sensitive to any residual soil coating remaining on the barrier layer's surface, the soil coating thickness can be chosen to maximize the response given by the sensor, but also to appropriately challenge the operation of a cleaning cycle. The third factor is the barrier layer thickness. In general, the thinner the barrier layer is the higher the sensitivity of the sensor. In some implementations, this particular factor can be used to fine tune the performance of the electronic indicator. The fourth factor is the spacing between adjacent electrodes, which is also referred to as electrode spacing (i.e., the length of L in FIG. 1B). In some cases, sensors with larger spacing have smaller capacitance but more extensive sensing fields and can probe thicker soil coating.

Figure 7A:
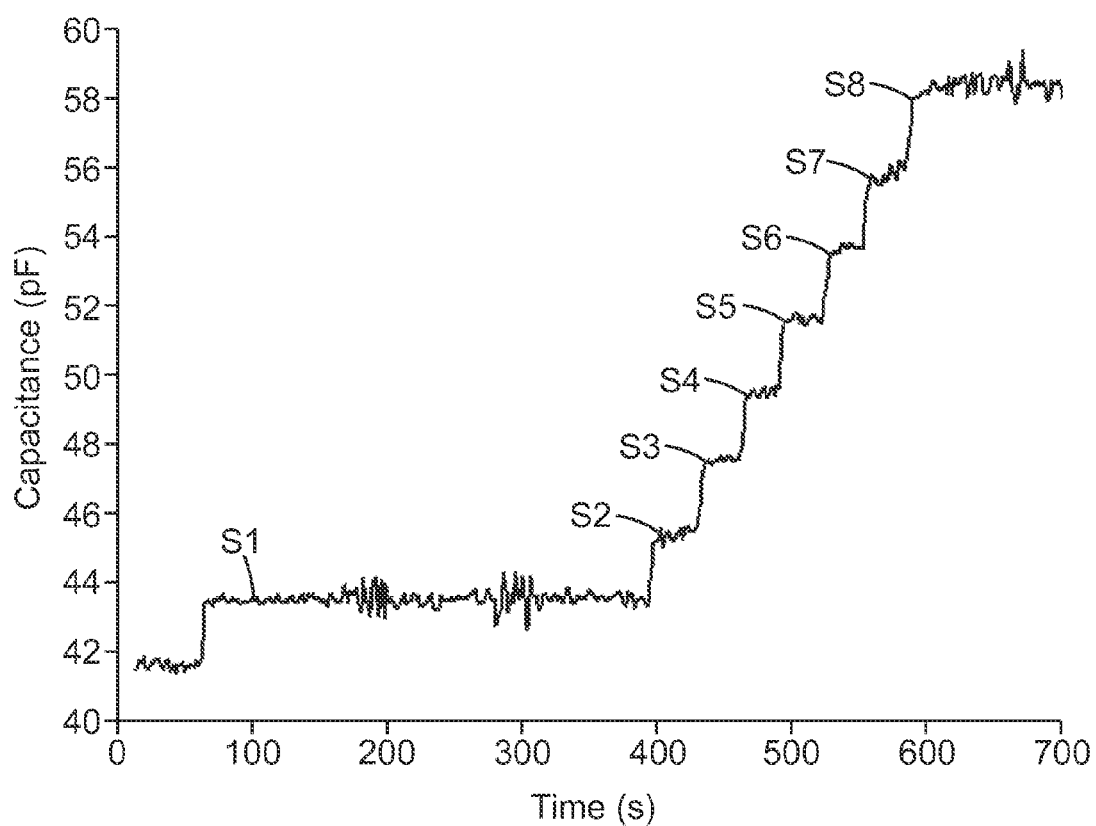
FIG. 7A illustrates a plot of capacitance versus time resulting from the sequential deposition of eight 10 µL drops of an artificial soil coating onto the active area of an electronic indicator.

In some embodiments, a capacitance of an electronic indicator can be measured to monitor efficacy of a cleaning cycle. FIG. 7A illustrates a plot of capacitance versus time resulting from the sequential deposition of eight 10 µL drops of an artificial soil onto the active area of an electronic indicator (as shown in FIG. 5). The plot illustrates the step changes (S1, S2, . . . S8) measured in capacitance as a drop of artificial soil is added to the electronic indicator's surface. The first drop of artificial soil is added at approximately 50 seconds, the second drop at approximately 400 seconds, and the remaining six drops at approximately 30 second intervals thereafter. As a specific example, capacitances can measured by an impedance analyzer (i.e., a Solartron Impedance/Gain-Phase Analyzer Model 1260, from Solartron Analytical, Hampshire, UK) applying 100 mV at 10 kHz across the interdigitated electrodes. The capacitance values can be calculated from imaginary impedances based on a serial resistor-capacitor circuit configuration.

Figure 7B:
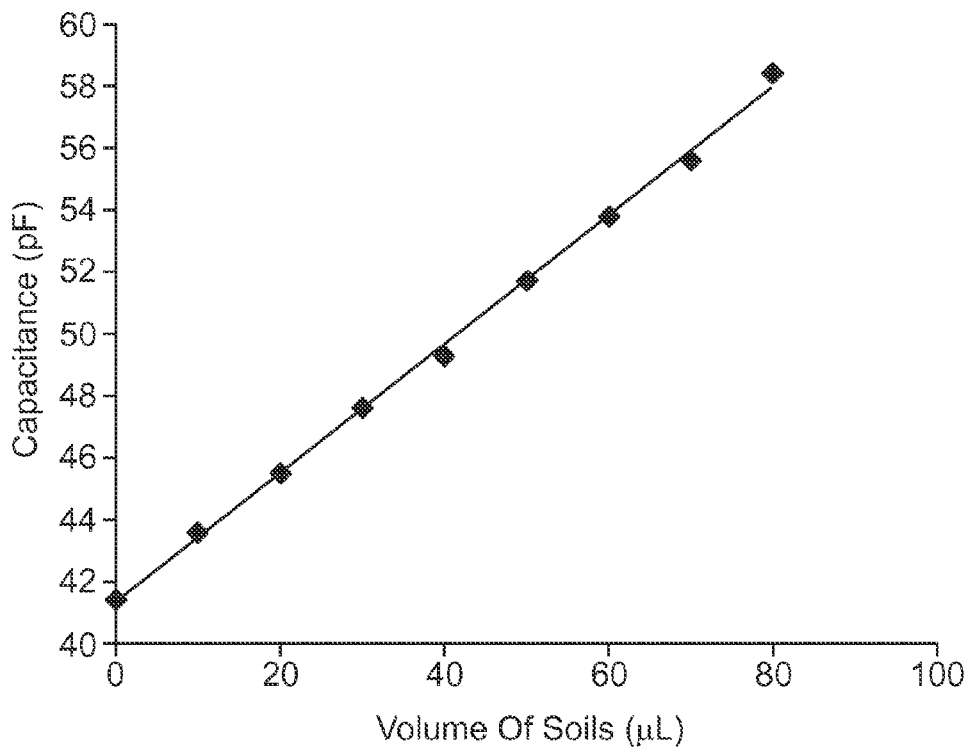
FIG. 7B shows a plot of capacitance versus the volume of artificial soil added to an electronic indicator's surface.

FIG. 7B shows a plot of capacitance versus the volume of soil added to an electronic indicator's surface, where the data is derived from the data in FIG. 7A. In some embodiments, the capacitance of the electronic indicator increases when the volume of artificial soil increases. In some cases, the increase in the capacitance is close to linearly proportional to the increase in the volume of the artificial soil. Similar to FIG. 7B, FIG. 7D illustrates a plot of total impedance verse the volume of soil added to the sensor's surface. In some embodiments, the total impedance of the electronic indicator decreases when the volume of artificial soil increases. In some cases, as illustrated in FIG. 7D, the decrease in the total impedance is close to linearly proportional to increase in the volume of the artificial soil.

Figure 7C:
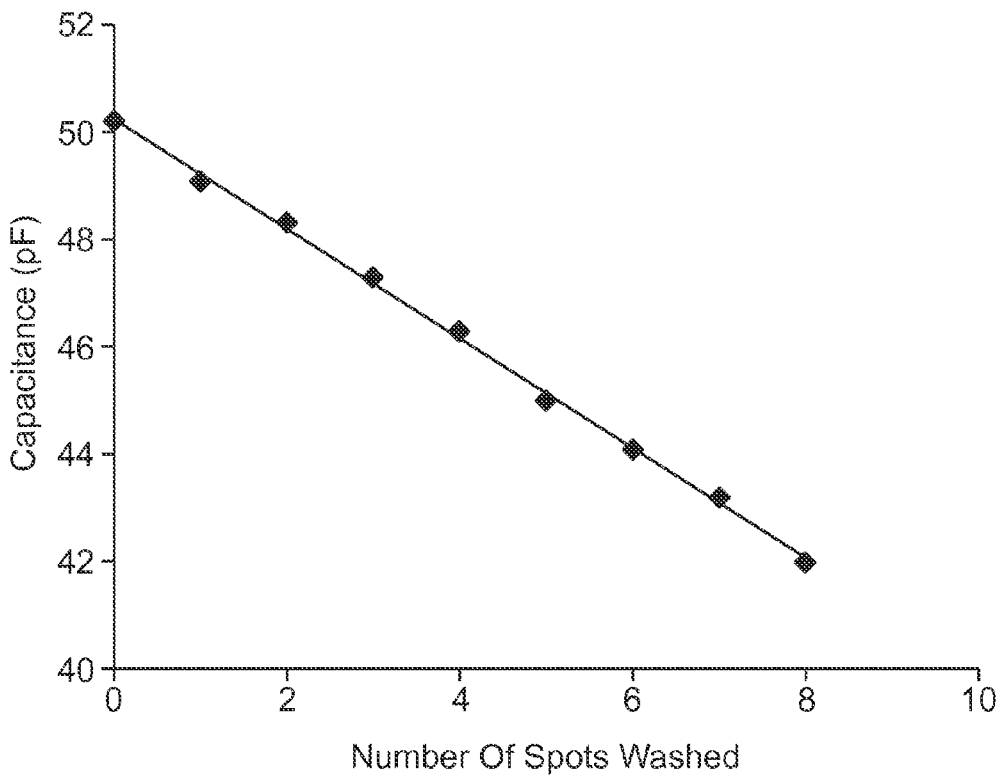
FIG. 7C shows changes in capacitance as soil spots on the electronic indicator are sequentially removed.
Figure 7D:
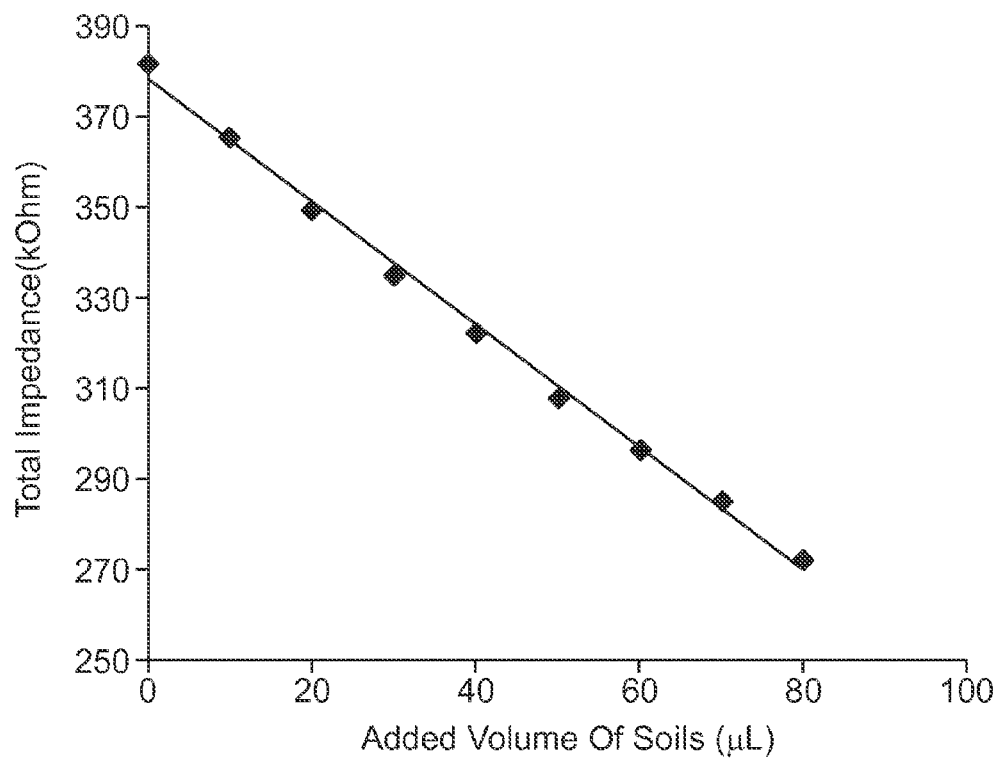
FIG. 7D illustrates a plot of total impedance verse the volume of soil added to the sensor's surface.

FIG. 7C shows changes in capacitance as soil spots on an electronic indicator (as illustrated in FIG. 5) are sequentially removed from the surface of the electronic indicator. For example, as a simulated study to evaluate the impact of soil volume to capacitance, cotton balls may be used to remove one soil spot at a time where the other spots were intact. In some embodiments, a decrease in capacitance due to the soil spots being removed can be observed. In some cases, as illustrated in FIG. 7B, the decrease in capacitance has generally linear or close to linear relationship with the amount of artificial soil being removed from the indicator surface. Because of this relationship, the electronic indicator can be used to determine the amount of residual artificial soil, if any, left on its surface after a cleaning cycle that can be used to determine efficacy of the cleaning cycle. Note that the initial value of the capacitance with eight soil spots is approximately 50 pF in FIG. 7C, while the ending value of the capacitance with eight soil spots is approximately 59 pF in FIG. 7B. This difference is because the soil spots are not completely dried when the capacitance is measured to generate the plot in FIG. 7B, where the soil spots are dried when the capacitance is measured to generate the plot in FIG. 7C.

Figure 7E:
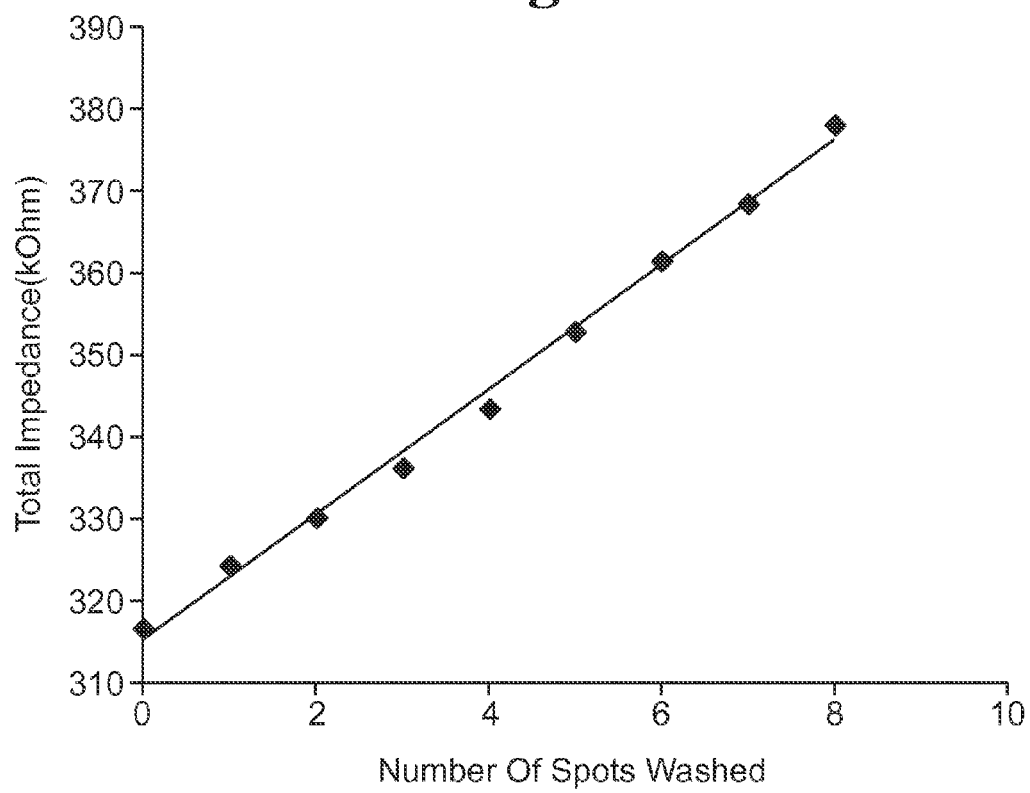
FIG. 7E shows changes in total impedance as soil spots on an electronic indicator are sequentially removed from the surface of the electronic indicator.

FIG. 7E shows changes in total impedance as soil spots on an electronic indicator (as illustrated in FIG. 5) are sequentially removed from the surface of the electronic indicator. In some embodiments, an increase in total impedance due to the soil spots being removed can be observed. In some cases, as illustrated in FIG. 7E, the increase in total impedance has generally linear or close to linear relationship with the amount of artificial soil being removed from the indicator surface. Because of this relationship, impedance of the electronic indicator can be measured to determine the amount of residual artificial soil, if any, left on its surface after a cleaning cycle that can be used to determine the efficacy of the cleaning cycle.

Figure 7F:
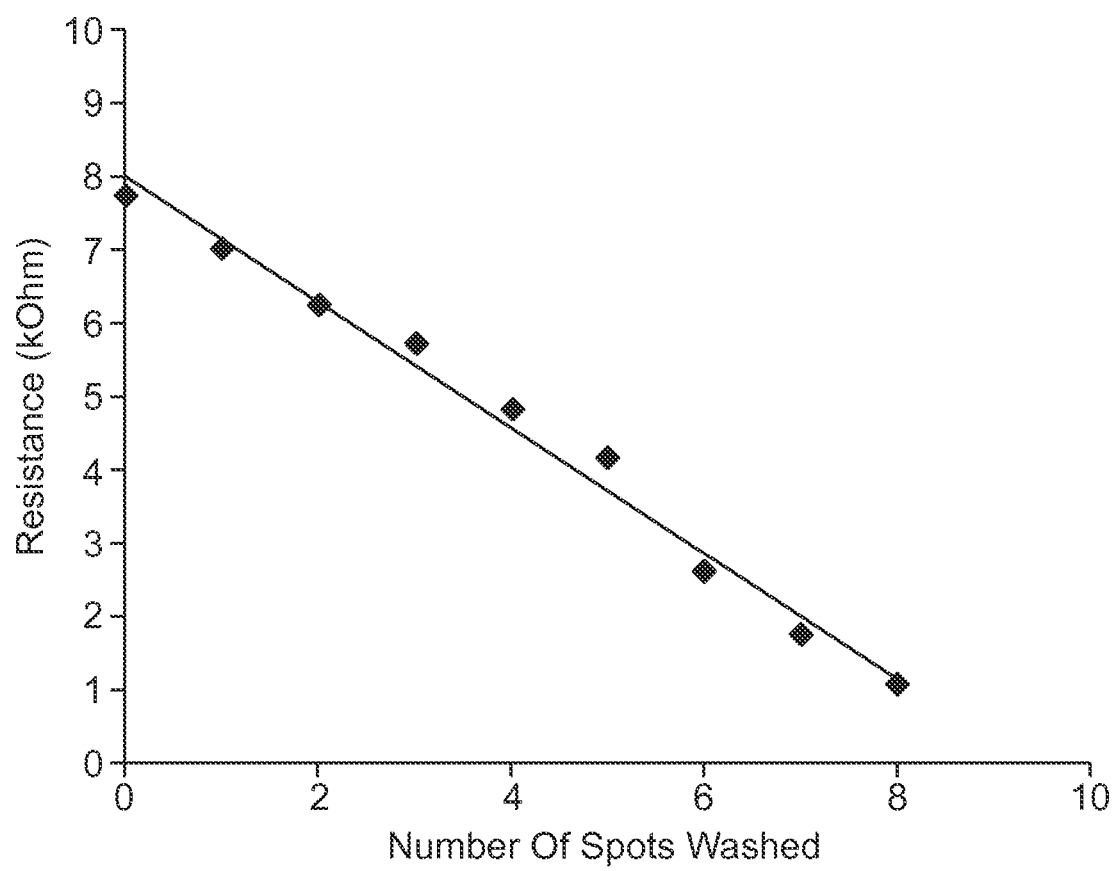
FIG. 7F shows changes in resistance as soil spots on an electronic indicator are sequentially removed from the surface of the electronic indicator.

FIG. 7F shows changes in resistance as soil spots on an electronic indicator (as illustrated in FIG. 5) are sequentially removed from the surface of the electronic indicator. In some embodiments, a decrease in resistance due to the soil spots being removed can be observed. In some cases, as illustrated in FIG. 7F, the decrease in resistance has generally linear or close to linear relationship with the amount of artificial soil being removed from the indicator surface. Because of this relationship, resistance of the electronic indicator can be measured to determine the amount of residual artificial soil, if any, left on its surface after a cleaning cycle that can be used to determine the efficacy of the cleaning cycle.

Figure 8:
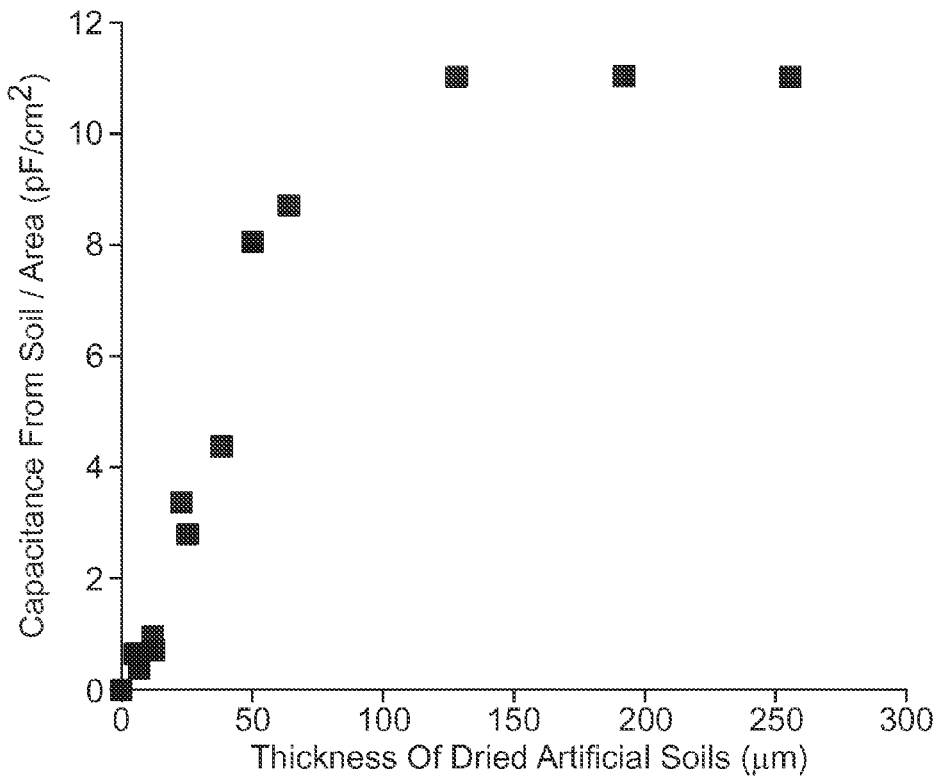
FIG. 8 shows the capacitance of an electronic indicator as a function of the thickness of an artificial soil coating.

FIG. 8 shows the capacitance of an electronic indicator as a function of the thickness of an artificial soil coating. In some embodiments, for a given electronic indicator configuration (i.e., a fixed barrier layer thickness, a fixed electrode spacing, etc.), the capacitance of the electronic indicator will increase with increased artificial soil coating thickness. When the thickness of the artificial soil coating is increased to a certain thickness, the electronic indicator's capacitance response is saturated. After the saturation point, further increases in the thickness of the soil coating have no effect. In some cases, the capacitance response is saturated because the soil coating thickness extends beyond the physical volume that the evanescent electric field is probing. In some embodiments, if capacitance response is used to evaluate efficacy of a cleaning cycle, electrical indicators can be constructed to have a selected thickness of artificial soil coating, so the indicators have appropriate sensitivity for wash monitoring and the capacitance response is not saturated.

This can be a particularly attractive feature of electronic indicators for wash and/or cleaning monitoring. This is because it allows the artificial soil coating thickness to be chosen primarily on the basis of what will provide an appropriate challenge to a given cleaning cycle without compromising the sensitivity of the electronic indicator (i.e., the thickness of the artificial soil coating is not too thick). This also allows the electronic indicator to be sensitive to any residual soil coating left on the sensor's surface as a result of an inadequate cleaning cycle. For the electronic indicator configurations whose capacitance response is shown in FIG. 8, the capacitance response saturates at a soil coating thickness of approximately 100 µm, with a peak response close to 10 pF/cm². In an exemplary embodiment, a capacitance measuring device that is capable of measuring with a resolution of 1 pF will be able to detect a thin residual soil coating, for example, a soil coating with thickness approximately 10 µm in the soil coated area of 1 cm².

Figure 9:
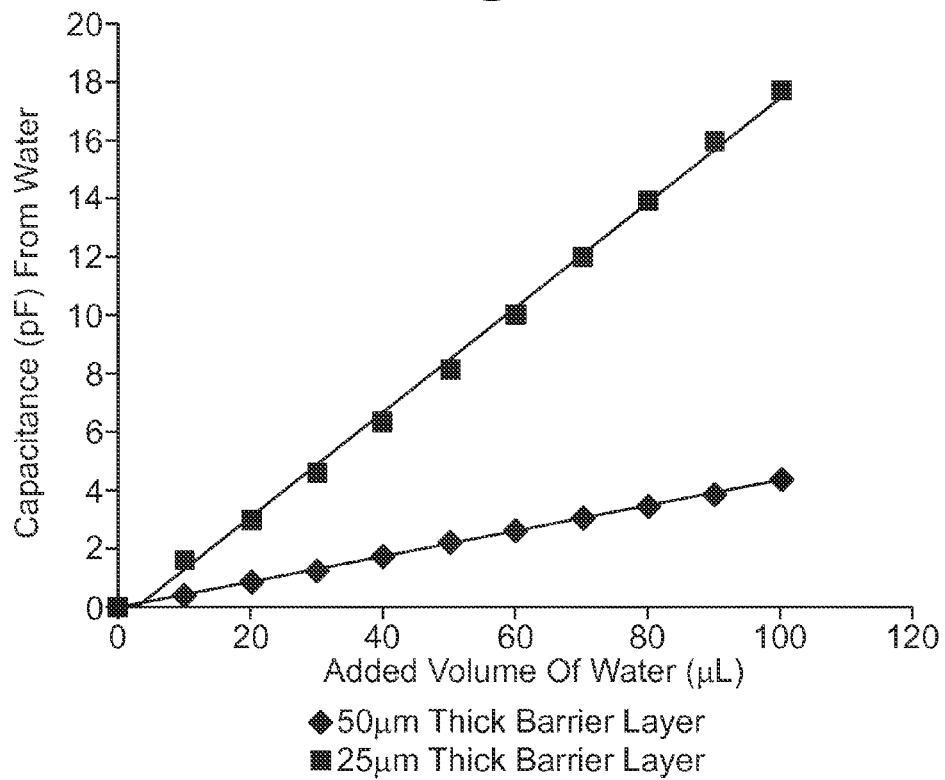
FIG. 9 shows the capacitance response of electronic indicators as a function of volume of water added to the surface of electronic indicators with different thickness of the barrier layer.

FIG. 9 shows the capacitance response of electronic indicators as a function of volume of water added to the surface of electronic indicators with different thickness of the barrier layer. The data shown compares two electronic indicators identical in design features with the exception of the barrier layer thickness (25 µm versus 50 µm). Water is added onto the active area of both indicators, with one drop at a time. In this experiment, each drop of water is 10 µL. As the surface area of the electronic indicator covered by water increases, the magnitude of the step change to the capacitance of the indicator (i.e., the difference between the capacitance for the indicator with 40 µL water on its surface and the capacitance for the indicator with 30 µL water on its surface) with 25 µm thick barrier layer is nearly 4 times higher than the step change to the indicator with 50 µm thick barrier layer. This indicates that an electronic indicator with 25 µm thick barrier layer is more sensitive to the change of water adding on the surface of the indicator than an electronic indicator with 50 µm thick barrier layer. This can be because the majority of the probing electric field for an electronic indicator with a thicker barrier layer (i.e., 50 µm) resides within the barrier layer itself. Hence, in some cases that capacitance of an electronic indicator is used to monitor efficacy of a cleaning cycle, an electronic indicator with a thinner barrier layer may be a preferred configuration.

Figure 10:
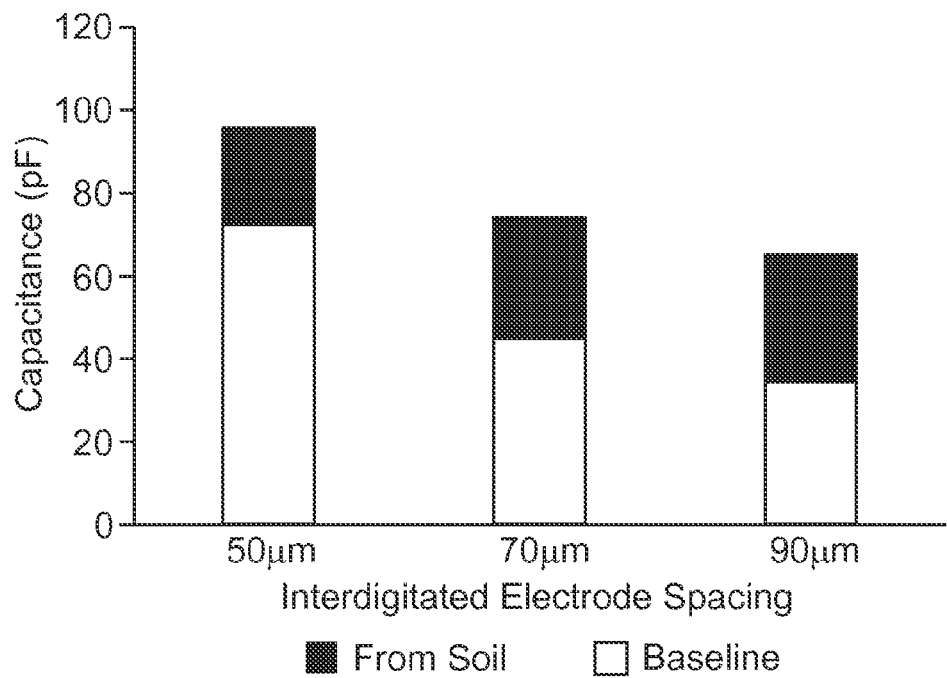
FIG. 10 shows the capacitance response of three electronic indicators, each with electrode spacing of 50 μm, 70 μm, and 90 μm respectively.

FIG. 10 shows the capacitance response of three electronic indicators, each with electrode spacing of 50 µm, 70 µm and 90 µm respectively. In some embodiments, the baseline capacitance of the electrical indicator (i.e., the capacitance measured when the indicator does not have artificial soil coated) is affected by the electrode spacing (i.e., when the electrode spacing increases, the baseline capacitance decreases).

Figure 11:
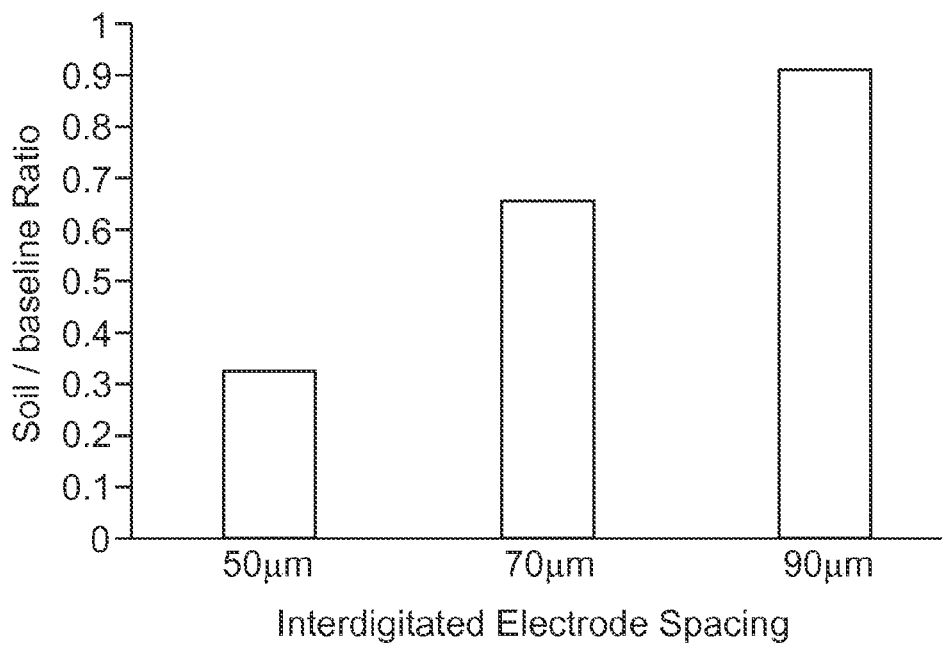
FIG. 11 shows a bar chart of (capacitance attributed to soil)/(baseline capacitance) ratio verse electrode spacing.
Figure 12:
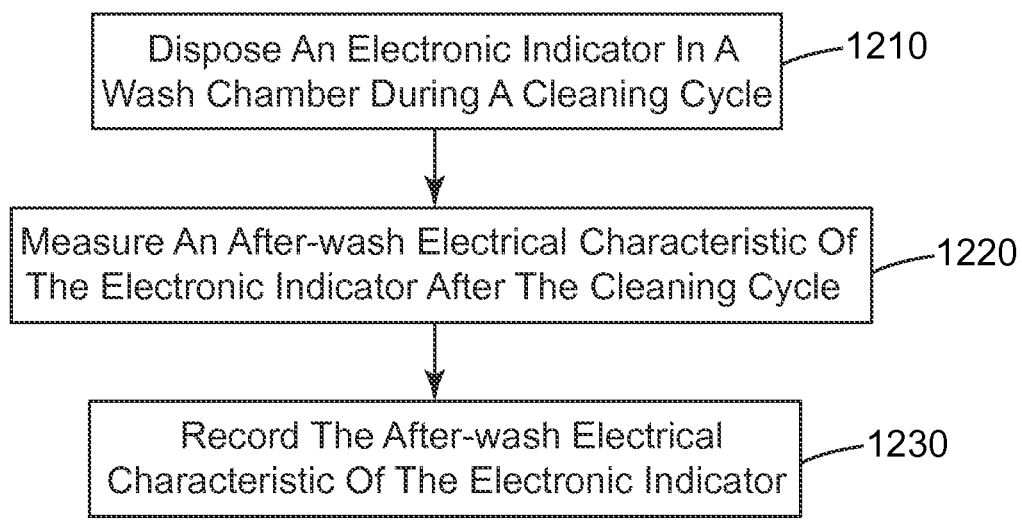
FIG. 12 shows a flow chart of the method for measuring wash efficacy using an embodiment of an electronic indicator of the present disclosure.

Furthermore, for a given thickness and area of soil coated on each of the three electronic indicators, when the electrode spacing increases, the capacitance attributable to the presence of the soil coating also increases. Thus, in some configurations, an electronic indicator with larger electrode spacing tends to have better sensitivity (i.e., a larger portion of capacitance is attributed to the artificial soil). FIG. 11 shows a bar chart of (capacitance attributed to soil)/(baseline capacitance) ratio, also referred to as soil/baseline ratio, verse electrode spacing. The soil/baseline ratio for a 90 µm electrode spacing electronic indicator is greater than 90%, while the soil/baseline ratio for a 50 µm electrode spacing electronic indicator is only about 30%.

EXAMPLES

Example 1

An electronic indicator, as illustrated in FIG. 5 was prepared an active area of metal (copper) traces of 2.44 cm×1.02 cm (i.e., active area of the electronic indicator); the spacing between individual metal traces (electrodes) was 75 µm and the width of individual metal traces was 75 µm. The barrier layer was a 25 µm thick KAPTON E brand polyimide film, available from Du Pont of Circleville, Ohio. The indicator was connected to impedance analyzer through copper tapes and additional wires. Transparent tape insulating layer was applied to cover and insulate copper electrodes. The insulating layer was SCOTCH brand Premium Heavy Duty Packaging Tape 3750, available from 3M Company of St. Paul, Minn. The indicator electrode was placed on a hot plate with the polyimide side up. The hot plate was maintained at a high temperature (60° C.) in order to expedite the drying process of deposited artificial soil. An artificial soil was prepared as a mixture of 9 mL sterile water added to a single vial of Artificial Test Soil ATS-9 available from Healthmark Industries Company, Inc., Fraser, Mich., USA. 10 µL of the artificial soil per spot was delivered to the electrode surface using a micropipette. The size of artificial soil spot was generally uniform. A plot of capacitance versus time resulting from the sequential deposition of eight 10 µL drops of an artificial soil onto the active area of the electronic indicator of Example 1 is illustrated in FIG. 7A. The plot of FIG. 7A illustrates the step changes (S1, S2, . . . S8) measured in capacitance as a drop of artificial soil was added to the electronic indicator's surface. The first drop of artificial soil is added at approximately 50 seconds, the second drop at approximately 400 seconds, and the remaining six drops were added at approximately 30 second intervals thereafter. The capacitances were measured by an impedance analyzer (i.e., a Solartron Impedance/Gain-Phase Analyzer Model 1260, from Solartron Analytical, Hampshire, UK) applying 100 mV at 10 kHz across the interdigitated electrodes. The capacitance values were calculated from imaginary impedances based on a serial resistor-capacitor circuit configuration.

FIG. 7B shows a plot of capacitance versus the volume of soil added to the electronic indicator's surface, of Example 1, where the data is derived from the data in FIG. 7A. In some embodiments, the capacitance of the electronic indicator increases when the volume of artificial soil increases. The increase in the capacitance is close to linearly proportional to the increase in the volume of the artificial soil. Similar to FIG. 7B, FIG. 7D illustrates a plot of total impedance verse the volume of soil added to the electronic indicator's surface. The total impedance of the electronic indicator decreased in a linearly proportional fashion when the amount of artificial soil increased.

FIG. 7C shows changes in capacitance as the number of soil spots on the electronic indicator Example 1 were sequentially removed from the surface of the electronic indicator using cotton balls to remove one soil spot at a time where the other spots were left intact. This simulated (in a controlled fashion) the removal of artificial soil during a cleaning cycle to which the electronic indicator would be subjected. The decrease in capacitance had a generally linear or close to linear relationship with the amount of artificial soil being removed from the indicator surface. Thus, the electronic indicator can be used to determine the amount of residual artificial soil, if any, left on its surface after a cleaning cycle that can be used to determine efficacy of the cleaning cycle. Note that the initial value of the capacitance with eight soil spots was approximately 50 pF in FIG. 7C, while the ending value of the capacitance with eight soil spots was approximately 59 pF in FIG. 7B. This difference was because the soil spots were not completely dried when the capacitance was measured to generate the plot in FIG. 7B, whereas the soil spots were dried when the capacitance was measured to generate the plot in FIG. 7C.

FIG. 7E shows changes in total impedance as soil spots on the electronic indicator of Example 1 were sequentially removed from the surface of the electronic indicator. As illustrated in FIG. 7E, the increase in total impedance was generally linear or close to a linear relationship with the amount of artificial soil that was removed from the indicator surface. Thus, impedance of the electronic indicator can be measured to determine the amount of residual artificial soil, if any, left on its surface after a cleaning cycle that can be used to determine the efficacy of the cleaning cycle.

FIG. 7F shows changes in resistance as soil spots on the electronic indicator of Example 1 were sequentially removed from the surface of the electronic indicator. As illustrated in FIG. 7F, the decrease in resistance was generally linear or close to a linear relationship with the amount of artificial soil being removed from the indicator surface. Thus, resistance of the electronic indicator can be measured to determine the amount of residual artificial soil, if any, left on its surface after a cleaning cycle that can be used to determine the efficacy of the cleaning cycle.

Example 2

Additional electronic indicators were prepared and measured in the same fashion as Example 1, but with different thicknesses of artificial soils coated onto the electrode. Table 1 and FIG. 8 show the capacitance of the electronic indicators of Example 2 as a function of the thickness of an artificial soil coating. The capacitance of the electronic indicator increased with increased artificial soil coating thickness. However, when the thickness of the artificial soil coating increased to a certain thickness, the electronic indicator's capacitance response was saturated. After the saturation point, further increases in the thickness of the soil coating had no effect. It is suggested that the capacitance response was saturated because the soil coating thickness extends beyond the physical volume that the evanescent electric field was probing. In Example 2 the capacitance response was saturated at a soil coating thickness of approximately 100 µm, with a peak response of about 10 pF/cm². Therefore, a capacitance measuring device that is capable of measuring with a resolution of 1 pF can detect a thin residual soil coating, even as thin as approximately 10 µm in the soil coated area of 1 cm².

Thus, if capacitance response is used to evaluate efficacy of a cleaning cycle, electrical indicators should be constructed to have a selected thickness of artificial soil coating, so that the indicators have appropriate sensitivity for wash monitoring and the capacitance response is not saturated. This can be a particularly attractive feature of electronic indicators for wash and/or cleaning monitoring. This is because it allows the artificial soil coating thickness to be chosen primarily on the basis of what will provide an appropriate challenge to a given cleaning cycle without compromising the sensitivity of the electronic indicator (i.e., the thickness of the artificial soil coating is not too thick). This also allows the electronic indicator to be sensitive to any residual soil coating left on the electronic indicator's surface as a result of an inadequate cleaning cycle.

TABLE 1

| Thickness of dried artificial soils (um) | Capacitance from soils/area (pF/cm²) |
|---|---|
| 0.0 | 0 |
| 6.0 | 0.61 |
| 6.8 | 0.40 |
| 12.0 | 0.91 |

TABLE 1-continued

| Thickness of dried artificial soils (um) | Capacitance from soils/area (pF/cm²) |
|---|---|
| 12.8 | 0.70 |
| 23.2 | 3.36 |
| 25.4 | 2.79 |
| 38.6 | 4.37 |
| 50.5 | 8.05 |
| 64.0 | 8.69 |
| 128.1 | 11.02 |
| 192.1 | 11.01 |
| 256.1 | 11.03 |

Example 3

Additional electronic indicators were prepared and measured in the same fashion as Example 1, but with two different thicknesses of the barrier layers, one with 25 μm thickness and the other with 50 μm barrier layer thickness. Both barrier layers were KAPTON E brand polyimide films, available from Du Pont. Water was added onto the active area of both indicator electrodes, one drop at a time, where each drop of water was 10 μL. FIG. 9 shows the capacitance response of the electronic indicators of Example 3 as a function of the volume of water added to the surface of electronic indicators with different thicknesses of the barrier layer. As the surface area of the electronic indicator covered by water increased, the capacitance also increased. It was noted that the rate of increase in capacitance with the addition of water (slope of the line) was higher for the electrode with the 25 μm thick barrier layer than it was for the electronic indicator with 50 μm think barrier layer. This indicates that the electronic indicator with 25 μm thick barrier layer is more sensitive to addition of water on the surface of the indicator than an electronic indicator with 50 μm thick barrier layer. This may be because the majority of the probing electric field for an electronic indicator with a thicker barrier layer (i.e., 50 μm) resides within the barrier layer itself.

Example 4

Example 4 electronic indicators were prepared and measured in the same fashion as Example 1, but with the following exceptions. The barrier layer was a 25 μm thick polyimide film, available from Multek Flexible Circuits, Inc. of Northfield, Minn. 200 μL of artificial soil was applied to 2.5 cm² of electrode area and then the indicators were dried at 60° C. for 20 minutes. The estimated thickness is 51.3 μm. Also three different metal trace thicknesses and spacing were used. The spacing between individual metal traces was 50 μm and the width of individual metal traces was 50 μm for Example 4A. spacing between individual metal traces was 70 μm and the width of individual metal traces was 70 μm for Example 4B. The spacing between individual metal traces was 90 μm and the width of individual metal traces was 90 μm for Example 4C. FIG. 10 shows the capacitance response of three electronic indicators of Example 4, each with electrode spacing of 50 μm, 70 μm and 90 μm respectively. The baseline capacitance of the electrical indicator (i.e., the capacitance measured when the indicator does not have artificial soil coated) was affected by the electrode spacing (i.e., when the electrode spacing increases, the baseline capacitance decreases).

Example 5

Example 5 electronic indicators were prepared and measured in the same fashion as Example 4, but with the exception that the SCOTCH Packaging Tape 3750 insulating layer was replaced with a tape made of silicone polyurea (SPU) adhesive on a polyester backing. The effects of electrode spacing on electronic indicator designs were further investigated. Table 2 shows the cycle parameters for an "adequate" wash cycle (i.e., the amount of residue soil is close to 0) in a GETINGE 46-4 model washer disinfector available from Getinge USA, Inc., Rochester, N.Y. Table 3 shows the capacitance of four replicate samples (S1-S4) of electronic indicators of Example 5A, 5B and 5C, with 50 μm, 70 μm and 90 μm electrode spacing, respectively, after an adequate wash cycle in the GETINGE washer-disinfector, as well as the baseline capacitance of the same electronic indicators (clean uncoated indicators).

TABLE 2

Adequate Wash Cycle Parameters

| Length | Process Step |
|---|---|
| 1.0 min. | Cold-water pre-rinse |
| 5.0 min. | Hot-water (60° C.) wash with detergent |
| 1.0 min. | Hot-water (60° C.) first rinse |
| 1.0 min. | Hot-water (60° C.) second rinse |
| 1.0 min. | Very-hot (90° C.) final rinse |
| 10.0 min. | Dry |

TABLE 3

Adequate Wash Cycle

| Electronic Indicator | Capacitance After Wash Cycle (pF) | Baseline Capacitance (pF) | ΔCapacitance (Baseline − After Wash Cycle) |
|---|---|---|---|
| Ex. 5A-S1 | 70.14 | 70.08 | −0.06 |
| Ex. 5A-S2 | 66.38 | 66.48 | 0.10 |
| Ex. 5A-S3 | 69.36 | 68.97 | −0.39 |
| Ex. 5A-S4 | 63.59 | 64.19 | 0.60 |
| Ex. 5B-S1 | 44.13 | 44.16 | 0.03 |
| Ex. 5B-S2 | 42.89 | 42.62 | −0.27 |
| Ex. 5B-S3 | 43.83 | 44.07 | 0.24 |
| Ex. 5B-S4 | 42.69 | 42.71 | 0.02 |
| Ex. 5C-S1 | 31.64 | 31.76 | 0.12 |
| Ex. 5C-S2 | 31.08 | 30.85 | −0.23 |
| Ex. 5C-S3 | 31.62 | 32.09 | 0.47 |
| Ex. 5C-S4 | 31.37 | 31.54 | 0.17 |

Table 4 shows the cycle parameters for an "inadequate" wash cycle (i.e., the amount of residue soil is inadequately large) in the GETINGE 46-4 model washer disinfector. Table 5 shows the capacitance of four different replicate samples (S5-S8) of electronic indicators of Example 5A, 5B and 5C, with 50 μm, 70 μm and 90 μm electrode spacing, respectively, after an inadequate wash cycle in the same washer-disinfector. Comparing the data in Table 3 and Table 5, the ΔCapacitance in an adequate wash cycle was generally smaller in value than ΔCapacitance in an inadequate wash cycle. Paired t-tests comparing adequate and inadequate wash cycles were conducted by each electrode spacing, 50 μm, 70 μm, and 90 μm respectively. Table 6 lists the resulting p-values. The p-values indicated the statistical confidence value of a difference between an adequate wash cycle and an inadequate wash cycle.

TABLE 4

Inadequate Wash Cycle Parameters

| Length | Process Step |
|---|---|
| 1.0 min. | Cold-water pre-rinse |
| 3.0 min. | Hot-water (60° C.) wash |
| 1.0 min. | Hot-water (60° C.) first rinse |
| 1.0 min. | Hot-water (60° C.) second rinse |
| 10.0 min. | Dry |

TABLE 5

Inadequate Wash Cycle

| Electronic Indicator | Capacitance After Wash Cycle (pF) | Baseline Capacitance (pF) | ΔCapacitance Baseline − After wash Cycle) |
|---|---|---|---|
| Ex. 5A-S5 | 63.72 | 63.98 | 0.26 |
| Ex. 5A-S6 | 68.47 | 67.59 | −0.88 |
| Ex. 5A-S7 | 65.06 | 65.46 | 0.40 |
| Ex. 5A-S8 | 64.37 | 63.82 | −0.55 |
| Ex. 5B-S5 | 41.47 | 41.82 | 0.35 |
| Ex. 5B-S6 | 43.14 | 42.58 | −0.56 |
| Ex. 5B-S7 | 43.45 | 42.18 | −1.27 |
| Ex. 5B-S8 | 42.50 | 41.85 | −0.65 |
| Ex. 5C-S5 | 30.76 | 30.18 | −0.58 |
| Ex. 5C-S6 | 30.72 | 30.59 | −0.13 |
| Ex. 5C-S7 | 31.15 | 30.36 | −0.79 |
| Ex. 5C-S8 | 30.97 | 30.49 | −0.48 |

TABLE 6

| Electronic Indicator | Electrode Spacing | Paired t-test p-value |
|---|---|---|
| Ex. 5A | 50 μm | 0.631 |
| Ex. 5B | 70 μm | 0.255 |
| Ex. 5C | 90 μm | 0.110 |

As observed in Table 6, the p-value decreases significantly as the electrode spacing is increased. For example, a p-value of 0.110 for electrode spacing of 90 μm indicates that close to 90% of cleaning monitoring tests will show a statistically significant difference between an adequate wash cycle and an inadequate wash cycle using electronic indicators having 90 μm electrode spacing. In comparison, a p-value of 0.631 for electrode spacing of 50 μm indicates that only about 40% of cleaning monitoring tests will show a statistically significant difference between an adequate wash cycle and an inadequate wash cycle using electronic indicators having 50 μm electrode spacing. This data indicates that electronic indicators with larger spacing can be a better choice for cleaning monitoring.

Example 6A

Example 6A electronic indicators were prepared and measured in the same fashion as Example 5C, with 90 μm electrode spacing and 90 μm widths of individual metal traces. The baseline capacitance of each uncoated electronic indicator in Example 6A was first measured prior to coating. An artificial test soil was prepared as follows. CEVOL brand polyvinyl alcohol polymer was obtained from Sekisui Specialty Chemicals (Secaucus, N.J.). A solution of FD&C Red Dye #40 was prepared by dissolving 160 mg of F&DC Red Dye #40 into 40 mL of sterile water. The 4 mg/mL Red Dye #40 solution was placed in a water bath at 80° C. CELVOL 425 polyvinyl alcohol polymer was added to each jar at a rate of about 1.0 gram/minute with stirring to obtain a final concentration of approximately 10 weight percent of the binder. The mixture was stirred for about one hour to allow the polymeric binder to fully dissolve. The final concentration of Red Dye #40 was 0.13 mg/mL, which was added primarily for visibility when coating the electronic indicators. Each electronic indicator of Example 6A was coated with 100 μL of the artificial test soil over the active area of each electronic indicator. The coated capacitance of each electronic indicator in Example 6A was measured after coating with the artificial test soil. The samples of Example 6A were divided into multiple sub-groups that were used to assess the wash disinfecting cycles of hospital grade commercial machines. Four different machines (M1, M2, M3, and M4), all of which were GETINGE DISINFECTION DECOMATT 8666 WASHER-DISINFECTORS, were used to process 9 loads (L1-L9) of instruments using two different wash disinfection cycles. The P1 cycle represented a "normal" load of surgical instruments and a regular wash cycle. The P2 cycle represented a heavy duty wash cycle and contained surgical instruments that were typically more soiled than those in the "normal" load. The electronic indicators were placed in baskets with the surgical instruments and the baskets were placed into the washer disinfection machines in one of 4 locations: T=top rack, 2=second rack down, 3=third rack down, and B=bottom rack. After the wash disinfection cycles, the electronic indicators were removed from the baskets and the final capacitance of each electronic indicator of Example 6A was measured. The % soil remaining on each electronic indicator was calculated using the following formula, where Final Capacitance was the capacitance after the wash disinfection cycle, Baseline Capacitance was the capacitance for each electronic indicator prior to coating with artificial test soil, and Coated Capacitance was the capacitance after coating with artificial test soil, but before exposure to the washer disinfection cycle. The variations in the percent soil remaining in Table 7 indicate the differences in load performance. All results in Table 7 are reported in % according to the calculation described below.

$$\% \text{ Soil Remaining} = \frac{(\text{Final Capactance} - \text{Baseline Capacitance})}{(\text{Coated Capacitance} - \text{Baseline Capacitance})}$$

TABLE 7

Percent Soil Remaining on Example 6A Electronic Indicators

| Load | Machine | Cycle | Top Rack | $2^{nd}$ Rack | $3^{rd}$ Rack | Bottom Rack |
|---|---|---|---|---|---|---|
| L1 | M4 | P1 | 6% | 10% | 4% | 9% |
| L2 | M2 | P1 | 3% | 11% | 4% | 0% |
| L3 | M1 | P2 | 9% | 8% | 8% | 15% |
| L4 | M4 | P2 | 9% | 6% | 16% | 10% |
| L5 | M2 | P2 | 2% | 5% | 3% | 7% |
| L6 | M3 | P2 | 14% | 11% | 9% | 32% |
| L7 | M1 | P2 | 0% | 4% | 9% | 11% |
| L8 | M3 | P2 | 18% | 16% | 12% | 11% |
| L9 | M1 | P1 | 17% | 0% | 3% | 27% |
| Average | — | — | 9% | 8% | 8% | 14% |
| STDEV | — | — | ±6 | ±5 | ±4 | ±10 |

Example 6B

Example 6B electronic indicators were prepared and measured in the same fashion as Example 6A, with 90 μm electrode spacing and 90 μm widths of individual metal traces. Example 6B samples were subjected to the adequate and inadequate wash cycles described in Tables 2 and 4 respectively using the GETINGE 46-4 model washer disinfector of Example 5. Electronic indicators of Example 6B were placed into the washer disinfection machine in one of 4 locations: T=top rack, M1=middle rack near the center of the washer, M2=middle rack near the periphery (outside wall) of the washer, and B=bottom rack. After the wash disinfection cycles, the electronic indicators were removed and the final capacitance of each electronic indicator of Example 6B was measured. Table 8 shows the % soil remaining results of the samples of Example 6B, calculated according the equation described in Example 6A.

TABLE 8

| Indicator Position | Adequate Wash Cycle % Soil Remaining | Inadequate Wash Cycle % Soil Remaining |
|---|---|---|
| Top | 7 | 25 |
| M1 | 4 | 39 |
| M2 | 2 | 39 |
| Bottom | 0 | 26 |

Example 7

The electronic indicator of Example 7 was prepared and measured in the same fashion as Example 6A, with 90 μm electrode spacing and 90 μm widths of individual metal traces. An amount of 100 μL of the artificial test soil, described in Example 6A, was coated over the active area of the electronic indicator. In addition, this electronic indicator had a set of lead wires permanently attached to the electrode contact pads that were hermetically sealed using an epoxy coating. The lead wires were approximately 91 cm long. This construction allowed for continuous simulated "remote" (91 cm distance away) measurement of the electronic indicator's capacitance while the electronic indicator was fully immersed in a solution. The wash disinfection cycle of an automated washer disinfector was simulated by using a glass beaker on a heated plate containing a series of rinse and wash solutions through the following sequence of steps:

1. Cold water wash (5 minutes)
2. Enzymatic detergent wash at 40° C. (15 minutes)
3. Hot water rinse at 70° C. (15 minutes)
4. Drying in hot air at 60° C. (1 hour)

All solutions were used under agitation using a magnetic stirrer. Step 4 was carried out in an oven held at a constant temperature of 60° C. For Step 2, 3M BMEC Enzymatic Detergent available from 3M Company of St. Paul, Minn. was used at a concentration specified in the manufacturer's instructions. The water used for all solution was reverse osmosis (RO) purified water.

Table 9 reports the capacitance measured in situ at the end of each step in the simulated wash and disinfection cycle. In addition, Table 9 also reports the baseline capacitance of the electronic indicator as well as the coated capacitance of the electronic indicator prior to the simulated wash and disinfection cycle, and the final capacitance of the electronic indicator 24 hours after completion of Step 4 in the simulated cycle. Five replicate measurements were made at each step and averaged together. All error bars are one standard deviation.

TABLE 9

In situ capacitance measured for a simulated wash and disinfection cycle

| Simulated Wash Disinfection Cycle Step | Solution | Temperature (° C.) | Time (minutes) | Capacitance (pF) |
|---|---|---|---|---|
| Baseline Capacitance | — | 22 | — | 43.8 ± 0.01 |
| Coated Capacitance | — | | | 58.3 ± 0.02 |
| Step 1 | RO water | 22 | 5 | 79.8 ± 0.12 |
| Step 2 | BMEC Enzymatic Detergent Wash | 40 | 15 | 86.5 ± 0.26 |
| Step 3 | RO water | 70 | 15 | 92.9 ± 1.32 |
| Step 4 | — | 60 | 60 | 50.3 ± 0.61 |
| Final Capacitance @ 24 Hours after Step 4 | — | 22 | — | 47.4 ± 0.02 |

Exemplary Embodiments

Embodiment One is an electronic indicator to monitor efficacy of a cleaning cycle, comprising:

a barrier layer comprising a first dielectric material, the barrier layer having a first barrier surface and a second barrier surface, the first barrier surface being opposite to the second barrier surface;

a volume of wash-removable artificial soil disposed on at least a portion of the first barrier surface; and a sensor having a first major sensor surface and an opposing second major sensor surface, wherein the first major sensor surface is adjacent to the second barrier surface, and wherein an electrical characteristic of the electronic indicator varies in response to a change in the volume of the artificial soil.

Embodiment Two is the electronic indicator of Embodiment One, wherein the sensor is configured to produce a sensor signal associated with the electrical characteristic of the electronic indicator when the electronic indicator is measured by an electrical characteristic reader.

Embodiment Three is the electronic indicator of Embodiment One or Two, wherein the sensor comprises an interdigitated electrode sensor.

Embodiment Four is the electronic indicator of Embodiment Three, wherein the interdigitated electrode sensor comprises three or more electrodes.

Embodiment Five is the electronic indicator of any one of the preceding Embodiments, further comprising an insulating layer comprising a second dielectric material and having a first insulating layer surface and an opposing second insulating layer surface, wherein the first insulating layer surface is adjacent to the second major sensor surface and covers at least a portion of the second major sensor surface.

Embodiment Six is the electronic indicator of Embodiment Five, further comprising a shielding layer comprising a conductive material disposed on at least a portion of the second insulating layer surface.

Embodiment Seven is the electronic indicator of any one of the preceding Embodiments, wherein the barrier layer has a thickness in the range of 5 nm to 5 mm.

Embodiment Eight is the electronic indicator of any one of the preceding Embodiments, wherein the electrical characteristic of the electronic indicator comprises at least one of capacitance characteristic, impedance characteristic, and conductance characteristic.

Embodiment Nine is a wash efficacy measurement system, comprising:
  an electronic indicator configured to be disposed in a wash chamber during a cleaning cycle, the electronic indicator comprising:
    a barrier layer comprising a dielectric material, the barrier layer having a first barrier surface and a second barrier surface, the first barrier surface being opposite to the second barrier surface;
    a volume of wash-removable artificial soil disposed on at least a portion of the first barrier surface; and
    a sensor having a first major sensor surface and an opposing second major sensor surface, wherein the first major sensor surface is adjacent to the second barrier surface,
    wherein the sensor is configured to produce a sensor signal associated with an electrical characteristic of the electronic indicator when the electronic indicator is measured by an electrical characteristic reader, and
    wherein the electrical characteristic of the electronic indicator varies in response to a change in the volume of the artificial soil, and
  an electrical characteristic reader configured to measure an after-wash electrical characteristic of the electronic indicator after the cleaning cycle, wherein the after-wash electrical characteristic of the electronic indicator indicates an efficacy of the cleaning cycle.

Embodiment Ten is the wash efficacy measurement system of Embodiment Nine, wherein the sensor comprises an interdigitated electrode sensor.

Embodiment Eleven is the wash efficacy measurement system of Embodiment Ten, wherein the interdigitated electrode sensor comprises two electrodes, and wherein the electrical characteristic reader is further configured to provide direct current or alternating current potentials to the two electrodes.

Embodiment Twelve is the wash efficacy measurement system of any one of the Embodiment Nine through Embodiment Eleven, wherein the electrical characteristic reader is further configured to measure a before-wash electrical characteristic of the electronic indicator without artificial soil before the cleaning cycle, wherein the efficacy of the cleaning cycle is determined based on the before-wash electrical characteristic of the electronic indicator and the after-wash electrical characteristic of the electronic indicator.

Embodiment Thirteen is the wash efficacy measurement system of any one of the Embodiment Nine through Embodiment Twelve, wherein the electrical characteristic reader is further configured to measure a before-wash electrical characteristic of the electronic indicator with artificial soil before the cleaning cycle, wherein the efficacy of the cleaning cycle is determined based on the before-wash electrical characteristic of the electronic indicator and the after-wash electrical characteristic of the electronic indicator.

Embodiment Fourteen is the wash efficacy measurement system of any one of the Embodiment Nine through Embodiment Thirteen, wherein the electrical characteristic of the electronic indicator comprises at least one of capacitance characteristic, impedance characteristic, and conductance characteristic.

Embodiment Fifteen is the wash efficacy measurement system of any one of the Embodiment Nine through Embodiment Fourteen, wherein the electrical characteristic reader is configured to the after-wash electrical characteristic during the cleaning cycle.

Embodiment Sixteen is the wash efficacy measurement system of Embodiment Fifteen, further comprising:
  a processor electronically coupled to the electrical characteristic reader, the processor configured to receive the after-wash electrical characteristic and generate a signal indicative of the efficacy of the cleaning cycle.

Embodiment Seventeen is an electronic indicator to monitor efficacy of a cleaning cycle, comprising:
  a barrier layer comprising a first dielectric material, the barrier layer having a first barrier surface and a second barrier surface, the first barrier surface being opposite to the second barrier surface;
  a volume of wash-removable artificial soil disposed on at least a portion of the first barrier surface;
  a sensor having a first major sensor surface and an opposing second major sensor surface, the first major sensor surface being adjacent to the second barrier surface; and
  an insulating layer comprising a second dielectric material and having a first insulating layer surface and an opposing second insulating layer surface,
  wherein the first insulating layer surface is adjacent to the second major sensor surface and covers at least a portion of the second major sensor surface, and
  wherein the electrical characteristic of the electronic indicator varies in response to a change in the volume of the artificial soil.

Embodiment Eighteen is a method for measuring wash efficacy, comprising:
  (1) disposing an electronic indicator in a wash chamber during a cleaning cycle, the electronic indicator comprising:
    a sensor configured to produce a sensor signal associated with an electrical characteristic of the electronic indicator, and
    a volume of wash-removable artificial soil disposed on at least a portion of a surface of the electronic indicator,
    wherein the electrical characteristic of the electronic indicator varies in response to a change in the volume of the artificial soil;
  (2) measuring an after-wash electrical characteristic of the electronic indicator after the cleaning cycle; and
  (3) recording the after-wash electrical characteristic of the electronic indicator.

Embodiment Nineteen is the method of Embodiment Eighteen, further comprising:
  determining an efficacy of the cleaning cycle based on the after-wash electrical characteristic of the electronic indicator.

Embodiment Twenty is the method of Embodiment Eighteen or Embodiment Nineteen, further comprising:
  measuring a before-wash electrical characteristic of the electronic indicator with artificial soil before the cleaning cycle,
  determining the efficacy of the cleaning cycle based on the before-wash electrical characteristic of the electronic indicator and the after-wash electrical characteristic of the electronic indicator.

Embodiment Twenty-one is the method of any one of the Embodiment Eighteen through Embodiment Twenty, further comprising:
  measuring a before-wash electrical characteristic of the electronic indicator without artificial soil before the cleaning cycle,
  determining the efficacy of the cleaning cycle based on the before-wash electrical characteristic of the electronic indicator and the after-wash electrical characteristic of the electronic indicator.

Embodiment Twenty-two is the method of any one of the Embodiment Eighteen through Embodiment Twenty-one, further comprising:

repeating steps (1) to (3) to collect a plurality of after-wash electrical characteristic of electronic indicators.

Embodiment Twenty-three is the method of the Embodiment Twenty-two, further comprising:

determining a threshold electrical characteristic based on the plurality of after-wash electrical characteristic of electronic indicators, wherein the threshold electrical characteristic is used to determine efficacy of a cleaning cycle.

Embodiment Twenty-four is the method of any one of the Embodiment Eighteen through Embodiment Twenty-three, further comprising:

comparing the after-wash electrical characteristic of the electronic indicator to an action limit, providing a signal indicative of a predefined action based on the comparison.

The present invention should not be considered limited to the particular examples and embodiments described above, as such embodiments are described in detail to facilitate explanation of various aspects of the invention. Rather the present invention should be understood to cover all aspects of the invention, including various modifications, equivalent processes, and alternative devices falling within the spirit and scope of the invention as defined by the appended claims.

What is claimed is:

1. An electronic indicator to monitor efficacy of a cleaning cycle, comprising:
   a barrier layer comprising a first dielectric material, the barrier layer having a first barrier surface and a second barrier surface, the first barrier surface being opposite to the second barrier surface;
   a volume of wash-removable artificial soil disposed on at least a portion of the first barrier surface; and
   a sensor having a first major sensor surface and an opposing second major sensor surface,
   wherein the first major sensor surface is adjacent to the second barrier surface, and
   wherein an electrical characteristic of the electronic indicator varies in response to a change in the volume of the artificial soil.

2. The electronic indicator of claim 1, wherein the sensor is configured to produce a sensor signal associated with the electrical characteristic of the electronic indicator when the electronic indicator is measured by an electrical characteristic reader.

3. The electronic indicator of claim 1, wherein the sensor comprises an interdigitated electrode sensor.

4. The electronic indicator of claim 3, wherein the interdigitated electrode sensor comprises three or more electrodes.

5. The electronic indicator of claim 1, further comprising an insulating layer comprising a second dielectric material and having a first insulating layer surface and an opposing second insulating layer surface, wherein the first insulating layer surface is adjacent to the second major sensor surface and covers at least a portion of the second major sensor surface.

6. The electronic indicator of claim 5, further comprising a shielding layer comprising a conductive material disposed on at least a portion of the second insulating layer surface.

7. The electronic indicator of claim 1, wherein the barrier layer has a thickness in the range of 5 nm to 5 mm.

8. The electronic indicator of claim 1, wherein the electrical characteristic of the electronic indicator comprises at least one of capacitance characteristic, impedance characteristic, and conductance characteristic.

9. A wash efficacy measurement system, comprising:
   an electronic indicator configured to be disposed in a wash chamber during a cleaning cycle, the electronic indicator comprising:
   a barrier layer comprising a dielectric material, the barrier layer having a first barrier surface and a second barrier surface, the first barrier surface being opposite to the second barrier surface;
   a volume of wash-removable artificial soil disposed on at least a portion of the first barrier surface; and
   a sensor having a first major sensor surface and an opposing second major sensor surface, wherein the first major sensor surface is adjacent to the second barrier surface,
   wherein the sensor is configured to produce a sensor signal associated with an electrical characteristic of the electronic indicator when the electronic indicator is measured by an electrical characteristic reader, and
   wherein the electrical characteristic of the electronic indicator varies in response to a change in the volume of the artificial soil; and
   an electrical characteristic reader configured to measure an after-wash electrical characteristic of the electronic indicator after the cleaning cycle starts, wherein the after-wash electrical characteristic of the electronic indicator indicates an efficacy of the cleaning cycle.

10. The wash efficacy measurement system of claim 9, wherein the sensor comprises an interdigitated electrode sensor.

11. The wash efficacy measurement system of claim 10, wherein the interdigitated electrode sensor comprises two electrodes, and wherein the electrical characteristic reader is further configured to provide direct current or alternating current potentials to the two electrodes.

12. The wash efficacy measurement system of claim 9, wherein the electrical characteristic reader is further configured to measure a before-wash electrical characteristic of the electronic indicator without artificial soil before the cleaning cycle, wherein the efficacy of the cleaning cycle is determined based on the before-wash electrical characteristic of the electronic indicator and the after-wash electrical characteristic of the electronic indicator.

13. The wash efficacy measurement system of claim 9, wherein the electrical characteristic reader is further configured to measure a before-wash electrical characteristic of the electronic indicator with artificial soil before the cleaning cycle, wherein the efficacy of the cleaning cycle is determined based on the before-wash electrical characteristic of the electronic indicator and the after-wash electrical characteristic of the electronic indicator.

14. The wash efficacy measurement system of claim 9, wherein the electrical characteristic of the electronic indicator comprises at least one of capacitance characteristic, impedance characteristic, and conductance characteristic.

15. The wash efficacy measurement system of claim 9, wherein the electrical characteristic reader is configured to the after-wash electrical characteristic during the cleaning cycle.

16. The wash efficacy measurement system of claim 15, further comprising:
   a processor electronically coupled to the electrical characteristic reader, the processor configured to receive the after-wash electrical characteristic and generate a signal indicative of the efficacy of the cleaning cycle.

17. An electronic indicator to monitor efficacy of a cleaning cycle, comprising:
- a barrier layer comprising a first dielectric material, the barrier layer having a first barrier surface and a second barrier surface, the first barrier surface being opposite to the second barrier surface;
- a volume of wash-removable artificial soil disposed on at least a portion of the first barrier surface;
- a sensor having a first major sensor surface and an opposing second major sensor surface, the first major sensor surface being adjacent to the second barrier surface; and
- an insulating layer comprising a second dielectric material and having a first insulating layer surface and an opposing second insulating layer surface,
- wherein the first insulating layer surface is adjacent to the second major sensor surface and covers at least a portion of the second major sensor surface, and
- wherein the electrical characteristic of the electronic indicator varies in response to a change in the volume of the artificial soil.

18. A method for measuring wash efficacy, comprising:
(1) disposing an electronic indicator in a wash chamber during a cleaning cycle, the electronic indicator comprising:
- a sensor configured to produce a sensor signal associated with an electrical characteristic of the electronic indicator, and
- a volume of wash-removable artificial soil disposed on at least a portion of a surface of the electronic indicator,
- wherein the electrical characteristic of the electronic indicator varies in response to a change in the volume of the artificial soil;

(2) measuring an after-wash electrical characteristic of the electronic indicator after the cleaning cycle; and (3) recording the after-wash electrical characteristic of the electronic indicator.

19. The method of claim 18, further comprising:
determining an efficacy of the cleaning cycle based on the after-wash electrical characteristic of the electronic indicator.

20. The method of claim 18, further comprising:
measuring a before-wash electrical characteristic of the electronic indicator with artificial soil before the cleaning cycle,
determining the efficacy of the cleaning cycle based on the before-wash electrical characteristic of the electronic indicator and the after-wash electrical characteristic of the electronic indicator.

21. The method of claim 18, further comprising:
measuring a before-wash electrical characteristic of the electronic indicator without artificial soil before the cleaning cycle,
determining the efficacy of the cleaning cycle based on the before-wash electrical characteristic of the electronic indicator and the after-wash electrical characteristic of the electronic indicator.

22. The method of claim 18, further comprising:
repeating steps (1) to (3) to collect a plurality of after-wash electrical characteristic of electronic indicators.

23. The method of claim 22, further comprising:
determining a threshold electrical characteristic based on the plurality of after-wash electrical characteristic of electronic indicators, wherein the threshold electrical characteristic is used to determine efficacy of a cleaning cycle.

24. The method of claim 18, further comprising:
comparing the after-wash electrical characteristic of the electronic indicator to an action limit,
providing a signal indicative of a predefined action based on the comparison.

* * * * *